(12) United States Patent
Snyder et al.

(10) Patent No.: US 11,426,242 B2
(45) Date of Patent: Aug. 30, 2022

(54) SYSTEM AND METHOD FOR REGISTRATION BETWEEN COORDINATE SYSTEMS AND NAVIGATION OF SELECTED MEMBERS

(71) Applicant: Medtronic Navigation, Inc., Louisville, CO (US)

(72) Inventors: Victor D. Snyder, Erie, CO (US); Brad Jacobsen, Erie, CO (US); Joseph Moctezuma, Golden, CO (US); Jerald Lamont Redmond, Germantown, TN (US); Katharine E. Darling, Arvada, CO (US); Justin Kemp, Erie, CO (US); Andrew Wald, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 710 days.

(21) Appl. No.: 16/261,882

(22) Filed: Jan. 30, 2019

(65) Prior Publication Data
US 2020/0237445 A1    Jul. 30, 2020

(51) Int. Cl.
  *A61B 34/20*    (2016.01)
  *A61B 34/30*    (2016.01)
  (Continued)

(52) U.S. Cl.
  CPC ............. *A61B 34/20* (2016.02); *A61B 34/30* (2016.02); *G06T 3/0068* (2013.01); *G06T 3/20* (2013.01);
  (Continued)

(58) Field of Classification Search
  CPC . A61B 17/1615; A61B 17/7032; A61B 17/86; A61B 2017/00725; A61B 2018/00339; A61B 2034/102; A61B 2034/105; A61B 2034/2051; A61B 2034/2055; A61B 2034/2057; A61B 2034/2065; A61B 2034/2068; A61B 2090/0818; A61B 2090/3762; A61B 2090/3983; A61B 2090/3995; A61B 34/20; A61B 34/30; G06T 2207/10116;
  (Continued)

(56) References Cited

U.S. PATENT DOCUMENTS 5,592,939 A    1/1997   Martinelli
5,913,820 A    6/1999   Bladen et al.
(Continued)

FOREIGN PATENT DOCUMENTS

WO    2013192598 A1    12/2013

OTHER PUBLICATIONS

International Search Report and Written Opinion dated May 14, 2020 in corresponding/related International Application No. PCT/US2020/015654.
(Continued)

*Primary Examiner* — Amelie R Davis
(74) *Attorney, Agent, or Firm* — Harness, Dickey & Pierce, P.L.C.

(57) ABSTRACT

Disclosed is a system for assisting in guiding and performing a procedure on a subject. The subject may be any appropriate subject such as inanimate object and/or an animate object. The guide and system may include various manipulable or movable members and may be registered to selected coordinate systems.

17 Claims, 11 Drawing Sheets

(51) Int. Cl.
    *G06T 7/11* (2017.01)
    *G06T 7/30* (2017.01)
    *G06T 3/00* (2006.01)
    *G06T 3/20* (2006.01)
    *G06T 7/20* (2017.01)

(52) U.S. Cl.
    CPC ............... *G06T 7/11* (2017.01); *G06T 7/20* (2013.01); *G06T 7/30* (2017.01); *A61B 2034/2051* (2016.02); *A61B 2034/2055* (2016.02); *A61B 2034/2057* (2016.02); *A61B 2034/2065* (2016.02); *A61B 2034/2068* (2016.02); *G06T 2207/10116* (2013.01); *G06T 2207/30012* (2013.01); *G06T 2207/30052* (2013.01); *G06T 2207/30196* (2013.01); *G06T 2207/30204* (2013.01)

(58) Field of Classification Search
    CPC . G06T 2207/30012; G06T 2207/30052; G06T 2207/30196; G06T 2207/30204; G06T 3/0068; G06T 3/20; G06T 7/11; G06T 7/20; G06T 7/30
    See application file for complete search history.

(56) References Cited

U.S. PATENT DOCUMENTS

| | | | |
|---|---|---|---|
| 5,983,126 | A | 11/1999 | Wittkampf |
| 6,474,341 | B1 | 11/2002 | Hunter et al. |
| 6,611,141 | B1 | 8/2003 | Schulz et al. |
| 6,940,941 | B2 | 9/2005 | Gregerson et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,751,865 | B2 | 7/2010 | Jascob et al. |
| 8,150,494 | B2 | 4/2012 | Simon et al. |
| 8,175,681 | B2 | 5/2012 | Hartmann et al. |
| 8,503,745 | B2 | 8/2013 | Simon et al. |
| 8,737,708 | B2 | 5/2014 | Hartmann et al. |
| 9,737,235 | B2 | 8/2017 | Hartmann |
| 2004/0199072 | A1 | 10/2004 | Sprouse et al. |
| 2009/0187194 | A1* | 7/2009 | Hamada ............ A61B 17/8897 606/104 |
| 2010/0228117 | A1 | 9/2010 | Hartmann |
| 2017/0231715 | A1 | 8/2017 | Roger et al. |
| 2018/0092699 | A1* | 4/2018 | Finley ............... A61B 17/7062 |
| 2018/0185113 | A1* | 7/2018 | Gregerson ............ A61B 6/032 |
| 2018/0325608 | A1 | 11/2018 | Kang et al. |
| 2019/0165885 | A1 | 5/2019 | Murakami et al. |

OTHER PUBLICATIONS

Invitation to Pay Additional Fees dated Apr. 24, 2020 in corresponding/related International Application No. PCT/US2020/015673.

Kirill Koulechov: "Leistungssteuerung chirurgischer Instrtumente in der Kopf-Chirurgie", Apr. 26, 2006, Technical University of Munich, Munich, Germany. Retrieved from the Internet: https://mediatum.ub.tum.de/doc/601976/601976.pdf.

Pfeiffer Jonas H et al: "A new module combining two tracking cameras to expand the workspace of surgical navigation systems", 2016 IEEE/SICE International Symposium on System Integration (SII), IEEE, Dec. 13, 2016, pp. 477-482, DOI 10.1109/SII.2016.784044.

International Search Report and Written Opinion dated Jun. 24, 2020 in corresponding/related International Application No. PCT/US2020/015673.

International Preliminary Report on Patenability and Written Opinion regarding International Application No. PCT/US2020/015673, dated Aug. 12, 2021.

* cited by examiner

SYSTEM AND METHOD FOR REGISTRATION BETWEEN COORDINATE SYSTEMS AND NAVIGATION OF SELECTED MEMBERS

CROSS-REFERENCE TO RELATED APPLICATIONS

This application includes subject matter similar to that disclosed in concurrently filed U.S. patent application Ser. No. 16/261,866. The entire disclosure of the above application is incorporated herein by reference.

FIELD

The subject disclosure is related generally to a tracking and navigation system, and particularly to registering coordinate systems for various procedures, such as navigating one or more members during a procedure.

BACKGROUND

This section provides background information related to the present disclosure which is not necessarily prior art.

An instrument can be navigated relative to a patient for performing various procedures. During a surgical procedure, an instrument can be tracked in a navigation or tracking space that may also be or include at least a portion of a patient space. A location of the instrument that is tracked can be displayed on a display device relative to an image of the patient.

The position of the patient can be determined with a tracking system. To track the patient relative to the image, however, generally, the patient is registered to the image, via tracking an instrument relative to the patient to generate a translation map between the subject or object space (e.g. patient space) and the image space. This often requires time during a surgical procedure for a user, such as a surgeon, to identify one or more points in the subject space and correlating, often identical points, in the image space.

After registration, the position of the instrument can be appropriately displayed on the display device while tracking the instrument. The position of the instrument relative to the subject can be displayed as a graphical representation, sometimes referred to as an icon on the display device.

SUMMARY

This section provides a general summary of the disclosure, and is not a comprehensive disclosure of its full scope or all of its features.

A system that allows for tracking of various members is disclosed. The system may track a plurality of members in a navigation or tracking space simultaneously. Each of the tracked members may be related to various portions, such as portions in an image. The image may be segmented to differentiate and delineate the portion to allow for substantially real time (e.g. minimal or no lag between real space movement and image representation) of a plurality of members in a navigation space. The navigation system may operate or receive tracking information from a plurality of tracking systems, including a first tracking system operating in a first tracking modality (e.g. electro-magnetic (EM)) and a second operating system operating in a second tracking modality (e.g. optical tracking).

To illustrate or navigate relative to an image, registration may occur between a selected physical space (e.g. subject space or navigation space) and an image space (e.g. defined by an image). According to various embodiments imageable fiducials may be used to perform registration. For example, a fiducial object can be imaged with an imaging system and can be identified or segmented in image data and image. The fiducial object may be connected to a selected system, such as a robotic system. The robotic system may include an appropriate robotic system, such as a Mazor X™ Robotic Guidance System, sold by Mazor Robotics Ltd. having a place of business in Israel and/or Medtronic, Inc. having a place of business in Minnesota, USA. The fiducial object may also be connected to a subject and/or position relative to a subject during an imaging procedure. Further, naturally occurring or inherent features of the subject may be identified as fiducial objects.

The fiducial object may include one or more objects, such as an array of discrete objects. The discrete objects may include spheres, objects of various shapes, a continuous and/or one or more rods that can all be in one or intersect one plane. The fiducial object can be modeled in three-dimensional (3D) space as a 3D model. Fiducial features can be extracted from the 3D model. The fiducial features can be compared to or coordinated with image fiducial features that result from the fiducial object or some portion thereof (e.g. an image fiducial feature can be a point relating to a center of a sphere or a circle or point relating to an intersection of a rod with a plane) being imaged.

Tracking device may have one or more tracking members that may be positioned within a navigation space to be tracked with one or more tracking systems. For example, a tracking member may be connected to one or more members or portions of a subject. A tracking member may be connected to a vertebrae or portion of a vertebrae of a patient. Similarly, a tracking device may be connected to one or more portions, such as a support beam, of any selected structure such as an automobile, air frame, cabinet system, or the like. Regardless, the tracking member is generally positioned in a fixed manner relative to a member or portion of the subject so that a relationship may be determined and used to allow for tracking the member in the navigation space by tracking the tracking member and determining the position of the connected member in the navigation space. Accordingly, one or more members may be tracked in a navigation space during a selected tracking procedure. Further, instruments may be positioned or moved into the navigation space that are separate from the subject, such as drills, awl, implant members, fasteners, or the like.

One or more tracking system may be incorporated into or operated with a navigation system that includes one or more instruments that may be tracked relative to the subject. The navigation system may include one or more tracking systems that track various portions, such as the tracking devices that may be associated with one or more members, such as boney portions, instruments, etc. The tracking system may include a localizer that is configured to determine the position of the tracking device in a navigation system coordinate system. Determination of the navigation system coordinate system may include those described at various references including U.S. Pat. Nos. 8,737,708; 9,737,235; 8,503,745; and 8,175,681; all incorporated herein by reference. In particular, a localizer may be able to track an object within a volume relative to the subject. The navigation volume, in which a device, may be tracked may include or be referred to as the navigation coordinate system or navigation space. A determination or correlation between the two coordinate systems may allow for or also be referred to as a registration between two coordinate systems.

Furthermore, images may be acquired of selected portions of a subject. The images may be displayed for viewing by a user, such as a surgeon. The images may have superimposed on a portion of the image a graphical representation of a tracked portion or member, such as an instrument. Also, various portions of the image may be segmented (e.g. boney members). According to various embodiments, the graphical representation may be superimposed on the image at an appropriate position due to registration of an image space (also referred to as an image coordinate system) to a subject space. A method to register a subject space defined by a subject to an image space may include those disclosed in U.S. Pat. Nos. 8,737,708; 9,737,235; 8,503,745; and 8,175,681; all incorporated herein by reference.

The graphical representation of a selected instrument, which may be separate from the subject, may be superimposed on the displayed image. The superimposed graphical representation may illustrate the position of the instrument that is tracked relative to the subject due to a registration of the subject or navigation space to the image space and tracking the instrument in the navigation space. Also, as noted above, tracking devices may be connected to various portions of the subject for reference of tracking members relative thereto and to each other. Segmented portions of the subject may be illustrated superimposed on the image and/or as portions of the image. Segmented portions of the image or graphical representations thereof may also be moved due to tracking the tracking devices that are on the various portions. The image, therefore, may be updated to include a representation of the tracked portion of the members (e.g. bony portions) due to tracking of the tracking devices.

During a selected procedure, the first coordinate system may be registered to the subject space or subject coordinate system due to a selected procedure, such as imaging of the subject. In various embodiments the first coordinate system may be registered to the subject by imaging the subject with a fiducial portion that is fixed relative to the first member or system, such as the robotic system. Due to registration of a second coordinate system to the first coordinate system may allow for tracking of additional elements not fixed to or tracked in the first coordinate system to a position determined or tracked within the first coordinate system and/or images of the subject.

The tracking of an instrument during a procedure, such as a surgical or operative procedure, allows for navigation of a procedure. When image data is used to define an image space it can be correlated or registered to a physical space defined by a subject, such as a patient. According to various embodiments, therefore, the patient defines a patient space in which an instrument can be tracked and navigated. The image space defined by the image data can be registered to the patient space defined by the patient. The registration can occur with the use of fiducials that can be identified in the image data and in the patient space.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The subject disclosure is directed to an exemplary embodiment of a surgical procedure on a subject, such as a human patient. It is understood, however, that the system and methods described herein are merely exemplary and not intended to limit the scope of the claims included herein. In various embodiments, it is understood, that the systems and methods may be incorporated into and/or used on non-animate objects. The systems may be used to, for example, to register coordinate systems between two systems for use on manufacturing systems, maintenance systems, and the like. For example, automotive assembly may use one or more robotic systems including individual coordinate systems that may be registered together for coordinated or consorted actions. Accordingly, the exemplary illustration of a surgical procedure herein is not intended to limit the scope of the appended claims.

Discussed herein, according various embodiments, are processes and systems for allowing registration between various coordinate systems. In various embodiments, a first coordinate system may be registered to a second coordinate system. The first coordinate system may be a first tracking space defined by a first tracking system having a first localizer and the second coordinate system may be a second tracking space defined by a second tracking system having a second localizer. Either or both of the first and second coordinate systems may be registered to additional coordinate systems or spaces (e.g. third coordinate system, fourth coordinate system, etc.). The additional coordinate systems may include an image coordinate system or space and/or subject coordinate system or space. As discussed herein, a navigation space or coordinate system may be defined relative to the subject space and by, at least in part, a tracking system space.

Figure 1:
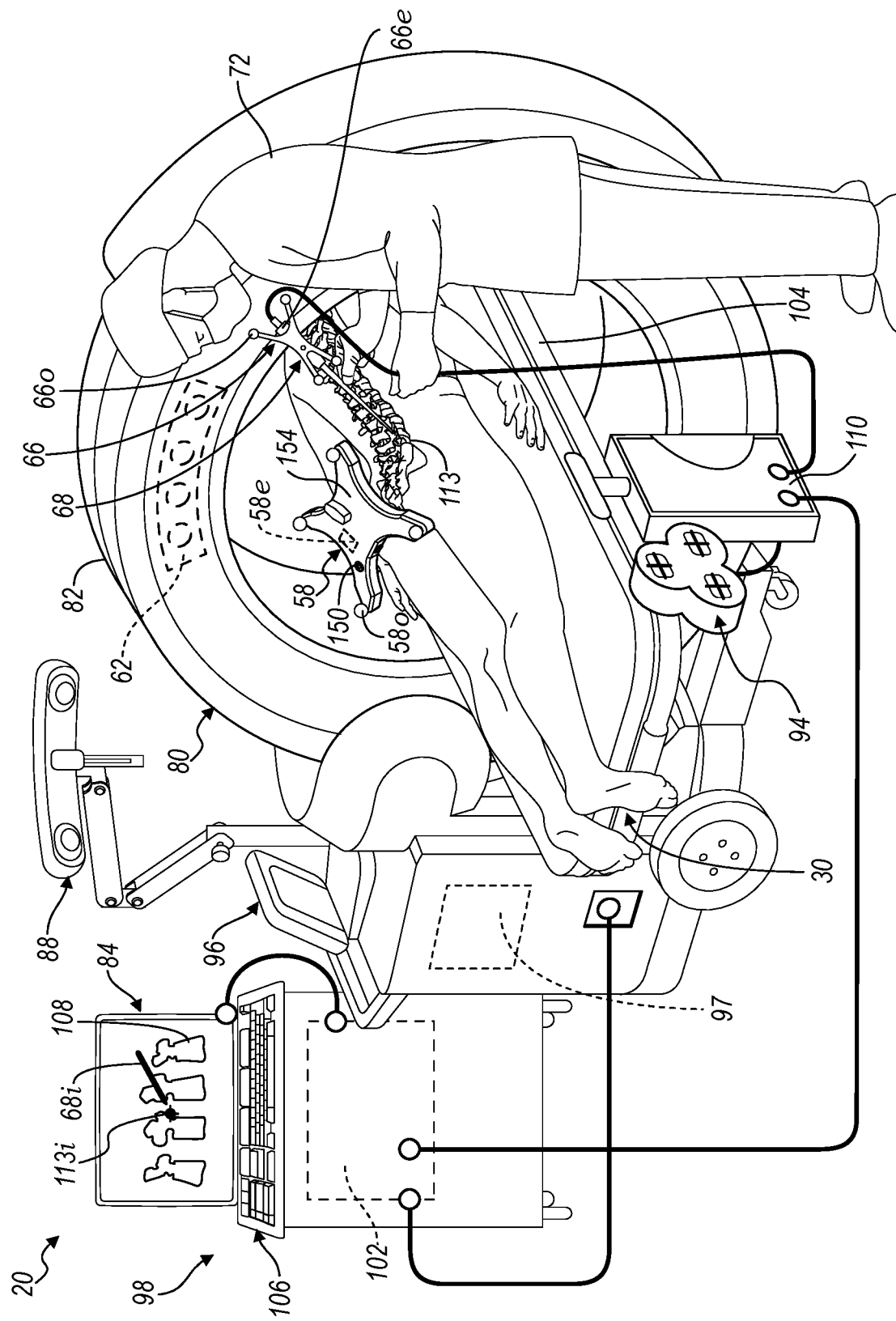
FIG. 1 is diagrammatic view illustrating an overview of a robotic system and a navigation system, according to various embodiments.

With initial reference to FIG. 1, a procedure theater, such as a surgical operating room, is illustrated. Positioned within the surgical theater may be various systems and members to be used during and/or assist in performing a procedure relative to the subject. For example, a navigation system 20 may be positioned within the operating theater. Within the operating theater, the navigation system 20 may include various elements or portions, such as an optical localizer 88 and an electromagnetic (EM) localizer 94, which define or are used to generate navigation or tracking spaces in selected first and/or second coordinate systems, as discussed further herein. The respective localizers 88, 94 may also be registered, also referred to as correlated, relative to one another, as also discussed further herein, to allow for tracking one or more instruments in either or both of the coordinate systems and relating the tracked position to an additional coordinate system. Accordingly, the user 72 may track one or more instruments, such as an instrument 68 relative to a subject 30 and/or track plurality of portions or members of the subject 30.

The navigation system 20 can be used to track the location of one or more tracking devices, tracking devices may include a subject tracking device 58, an imaging system tracking device 62, and/or a tool tracking device 66. The tool 68 may be any appropriate tool such as a drill, forceps, or other tool operated by the user 72. The tool 68 may also include an implant, such as a spinal implant or orthopedic implant. It should further be noted that the navigation system 20 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 20 and the various instruments may be used in any appropriate procedure, such as one that is generally minimally invasive or an open procedure.

An imaging device 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-arm® imaging device sold by Medtronic Navigation, Inc. having a place of business in Louisville, Colo., USA. The imaging device 80 may have a generally annular gantry housing 82 in which an image capturing portion is moveably placed. The imaging device 80 may acquire image data with x-rays. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 80 to be acquired from multiple directions or in multiple planes. The imaging device 80 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 80 can utilize flat plate technology having a 1,720 by 1,024 pixel viewing area.

The position of the imaging device 80, and/or portions therein such as the image capturing portion, can be precisely known relative to any other portion of the imaging device 80. The imaging device 80, according to various embodiments, can know and recall precise coordinates relative to a fixed or selected coordinate system. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

The imaging device 80 can also be tracked with the tracking device 62. The image data defining an image space acquired of the patient 30 can, according to various embodiments, be inherently or automatically registered relative to an object space. The object space can be the space defined by the patient 30 in the navigation system 20. The automatic registration can be achieved by including the tracking device 62 on the imaging device 80 and/or the determinable precise location of the image capturing portion. According to various embodiments, as discussed herein, imageable portions, virtual fiducial points and other features can also be used to allow for registration, automatic or otherwise. It will be understood, however, that image data can be acquired of any subject which will define subject space. Patient space is an exemplary subject space. Registration allows for a translation between patient space and image space.

The patient 80 can also be tracked as the patient moves with a patient tracking device (also referred to as a dynamic reference frame (DRF)) or tracker 58. Alternatively, or in addition thereto, the patient 30 may be fixed within navigation space defined by the navigation system 20 to allow for registration. As discussed further herein, registration of the image space to the patient space or subject space allows for navigation of the instrument 68 with the image data. When navigating the instrument 68, a position of the instrument 68 can be illustrated relative to image data acquired of the patient 30 on a display device 84. Various tracking systems, such as one including the optical localizer 88 or the electromagnetic (EM) localizer 92 can be used to track the instrument 68.

More than one tracking system can be used to track the instrument 68 in the navigation system 20. According to various embodiments, these can include an electromagnetic tracking (EM) system having the EM localizer 94 and/or an optical tracking system having the optical localizer 88. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated. It is further understood that additional or alternative tracking systems may also be used, such as radar, acoustic, ultrasonic, and/or other tracking systems. Generally, the tracking system tracks the tracking device in the tracking or navigation space. The tracking system is able to generate a signed based on the tracking (e.g. within a field of view of a camera, EM field, etc.) and the signal is used within the navigation system to determine the position of the tracked element. In various embodiments, the determined position may then be illustrated on a display device relative to another coordinate system, such as image space.

It is further appreciated that the imaging device 80 may be an imaging device other than the O-arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In various embodiments, an imaging device controller 96 may control the imaging device 80 and can receive the image data generated at the image capturing portion and store the images for later use. The controller 96, in various embodiments, may include a processor 97 and/or various memory portions. The controller 96 can also control the rotation of the image capturing portion of the imaging device 80. It will be understood that the controller 96 need not be integral with the gantry housing 82, but may be separate therefrom. For example, the controller may be a portions of the navigation system 20 that may include a processing and/or control system 98 including a processing unit or processing portion 102. The controller 96, however, may be integral with the gantry 82 and may include the second and separate processor 97, such as that in a portable computer.

The patient 30 can be fixed onto an operating table 104. According to one example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 30 relative to the imaging device 80 can be determined by the navigation system 20. The tracking device 62 can be used to track and locate at least a portion of the imaging device 80, for example the gantry or housing 82. The patient 30 can be tracked with the dynamic reference frame 58, as discussed further herein. Accordingly, the position of the patient 30 relative to the imaging device 80 can be determined. Further, the location of the imaging portion can be determined relative to the housing 82 due to its precise position on the rail within the housing 82, substantially inflexible rotor, etc. The imaging device 80 can include an accuracy of within 10 microns, for example, if the imaging device 80 is an O-Arm® imaging device sold by Medtronic Navigation, Inc. having a place of business in Louisville, Colo. Precise positioning of the imaging portion is further described in U.S. Pat. Nos. 7,188,998; 7,108,421; 7,106,825; 7,001,045; and 6,940,941; all of which are incorporated herein by reference, According to various embodiments, the imaging device 80 can generate and/or emit x-rays from the x-ray source that propagate through the patient 30 and are received by the x-ray imaging receiving portion. The image capturing portion generates image data representing the intensities of the received x-rays. Typically, the image capturing portion can include an image intensifier that first converts the x-rays to visible light and a camera (e.g. a charge couple device) that converts the visible light into digital image data. The image capturing portion may also be a digital device that converts x-rays directly to digital image data for forming images, thus potentially avoiding distortion introduced by first converting to visible light.

Two dimensional and/or three dimensional fluoroscopic image data that may be taken by the imaging device 80 can be captured and stored in the imaging device controller 96. Multiple image data taken by the imaging device 80 may also be captured and assembled to provide a larger view or image of a whole region of a patient 30, as opposed to being directed to only a portion of a region of the patient 30. For example, multiple image data of the patient's 30 spine may be appended together to provide a full view or complete set of image data of the spine.

The image data can then be forwarded from the image device controller 96 to the navigation computer and/or processor system 102 that can be a part of a controller or work station 98 having a display 84 and a user interface 106. It will also be understood that the image data is not necessarily first retained in the controller 96, but may also be directly transmitted to the work station 98. The work station 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, via the image device controller 96, or adjust the display settings of the display 84. The work station 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 20 can further include the tracking system which may be one or both of the electromagnetic (EM) localizer 94 and/or the optical localizer 88. As noted above, however, more or alternative tracking systems may also be provided or used. The tracking systems may include a controller and interface portion 110. The controller 110 can be connected to the processor portion 102, which can include a processor included within a computer. The controller 110 may also be connected to one or more of the localizers, such as the EM localizer 94 and/or the optical localizer 88. The connections may be wired or wireless and allow for single or two-way communication. The EM tracking system may include the STEALTHSTATION® AXIEM™ Navigation System, sold by Medtronic Navigation, Inc. having a place of business in Louisville, Colorado; or can be the EM tracking system described in U.S. Pat. No. 7,751,865, issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 20 may also be or include any appropriate tracking system, including a STEALTHSTATION® TREON® or S7™ tracking systems having an optical localizer, that may be used as the optical localizer 88, and sold by Medtronic Navigation, Inc. of Louisville, Colorado. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller 110. Also, the tracking devices 62, 66, 154 can generate a field and/or signal that is sensed by the localizer(s) 88, 94.

Various portions of the navigation system 20, such as the instrument 68, and others as will be described in detail below, can be equipped with at least one, and generally multiple, of the tracking devices 66. The instrument can also include more than one type or modality of tracking device 66, such as an EM tracking device 66e and/or an optical tracking device 66o. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 20, therefore, may be a hybrid system that includes components from various tracking systems.

According to various embodiments, the navigation system 20 can be used to track the instrument 68 relative to the patient 30. The instrument 68 can be tracked with the tracking system, as discussed above. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a translation map to be generated of the physical location of the instrument 68 relative to the image space of the image data. The translation map allows the tracked position of the instrument 68 to be displayed on the display device 84 relative to the image data 108. A graphical representation 68i, also referred to as an icon, can be used to illustrate the location of the instrument 68 relative to the image data 108.

As discussed above, the imaging system 80, or any appropriate imaging system, may acquire images of the subject 30. The images may be automatically registered, according to various procedures such as those known in the art, including tracking the imaging system 80 (e.g. with the image tracking device 62) and tracking the subject 30 with the subject tracker 58. Other registration processes may include identifying fiducial or correlation points in the image 108 and on the patient or subject 30. Fiducial points may include artificial fiducials that are imageable portions (e.g. radiopaque markers) that are positioned on and/or implanted in the subject 30 during acquisition of images with the imaging device 80 and appear on the image 108, such as a fiducial mark 113. The user 72 may identify the fiducial mark 113 in the image 108 and then also identify the fiducial on the subject 30, such as touching the fiducial in the subject with the instrument 68 that is tracked with one or more of the tracking systems. The navigation system 20 may then determine the position of the tracked instrument 68 and correlated it with the fiducial 113 identified in the image 108.

In various embodiments, when the fiducial portions 113 are imaged with the imaging device 80, image data is generated that includes or identifies the fiducial portions 113. The fiducial portions 113 can be identified in image data as imaged fiducial portions 113i automatically (e.g. with a processor executing a program), manually (e.g. by selection an identification by the user 72), or combinations thereof (e.g. by selection an identification by the user 72 of a seed point and segmentation by a processor executing a program). Methods of automatic imageable portion identification include those disclosed in U.S. Pat. No. 8,150,494 issued on Apr. 3, 2012, incorporated herein by reference. Manual identification can include selecting an element (e.g. pixel) or region in the image data wherein the imageable portion has been imaged. Regardless, the fiducial portions 113 identified in the image data can be used as fiducial points or positions that can be used to register the image data or the image space of the image data with patient space.

In various embodiments, to register an image space or coordinate system to another space or coordinate system, such as a navigation space, the fiducial portions 113 that are identified in the image 108 may then be identified in the subject space defined by the subject 30, in an appropriate manner. For example, the user 72 may move the instrument 68 relative to the subject 30 to touch the fiducial portions 113, if the fiducial portions are attached to the subject 30 in the same position during the acquisition of the image data to generate the image 108. It is understood that the fiducial portions 113, as discussed above in various embodiments, may be attached to the subject 30 and/or may include anatomical portions of the subject 30.

Additionally, a tracking device may be incorporated into the fiducial portions 113 and they may be maintained with the subject 30 after the image is acquired. In this case, the registration or the identification of the fiducial portions 113 in a subject space may be made. Nevertheless, according to various embodiments, the user 72 may move the instrument 68 to touch the fiducial portions 113. The tracking system, such as with the optical localizer 88, may track the position of the instrument 68 due to the tracking device 66 attached thereto. This allows the user 72 to identify in the navigation space the locations of the fiducial portions 113 that are identified in the image 108. After identifying the positions of the fiducial portions 113 in the navigation space, which may include a subject space, the translation map may be made between the subject space defined by the subject 30 in a navigation space and the image space defined by the image 108. Accordingly, identical or known locations allow for registration as discussed further herein.

During registration, a translation map is determined between the image data coordinate system of the image data such as the image 108 and the patient space defined by the patient 30. Once the registration occurs, the instrument 68 can be tracked with the tracking system that is registered to the image data to allow an identification and illustration of a position of the tracked instrument 68 as an icon superimposed on the image data. Registration of the image 108 (or any selected image data) to the subject 30 may occur at any appropriate time.

After the registration of the image space to the patient space, the instrument 68 can be tracked relative to the image 108. As illustrated in FIG. 1, the icon 68i representing a position (which may include a 6 degree of freedom position (including 3D location and orientation)) of the instrument 68 can be displayed relative to the image 108 on the display 84. Due to the registration of the image space to the patient space, the position of the icon 68i relative to the image 108 can substantially identify or mimic the location of the instrument 68 relative to the patient 30 in the patient space. As discussed above, this can allow a navigated procedure to occur.

Figure 2:
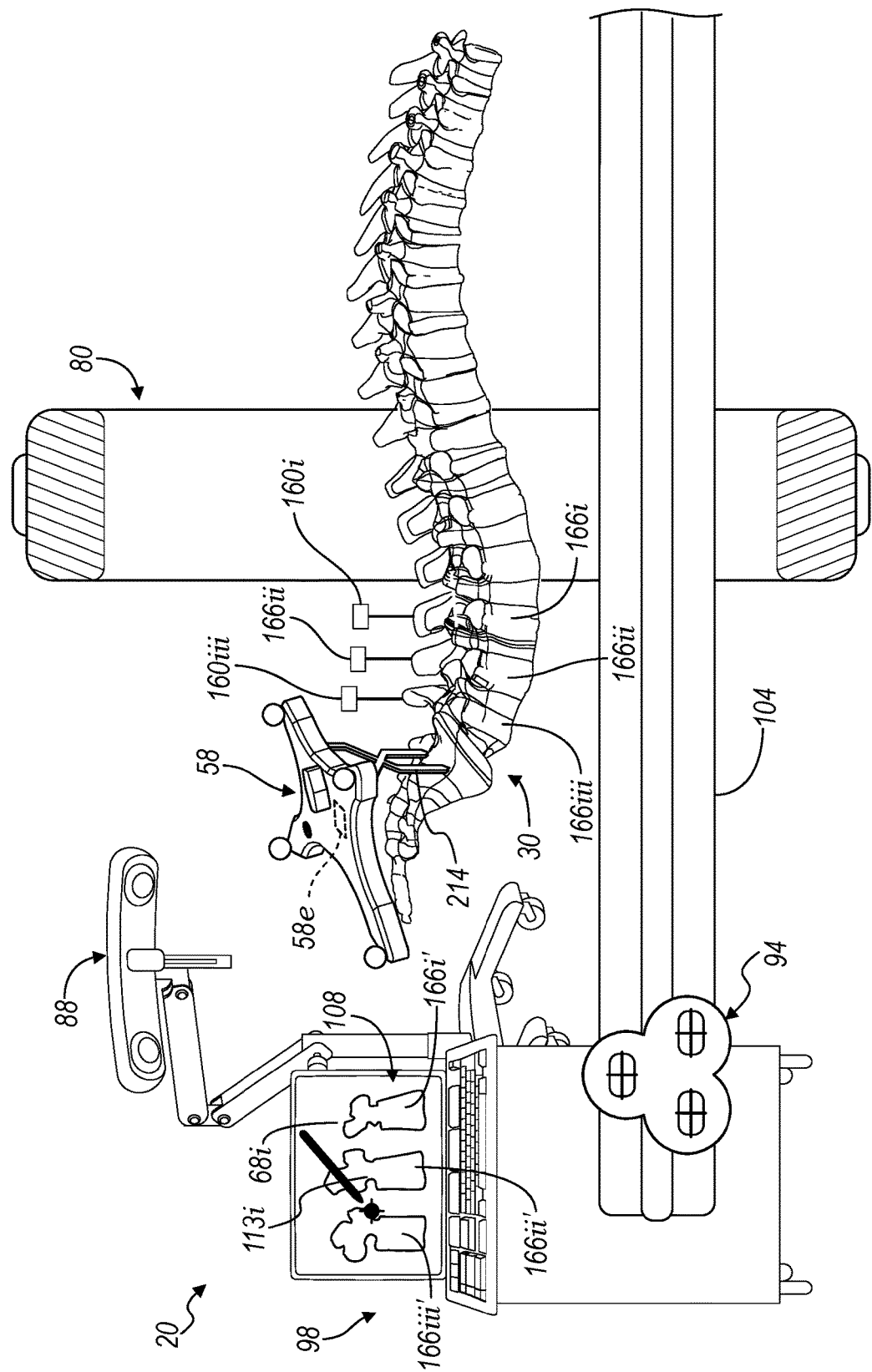
FIG. 2 is a detailed environmental view of a tracking system, according to various embodiments.

With continuing reference to FIG. 1 and FIG. 2, the patient tracker or subject tracker 58 may also include more than one tracking element or portion and/or be operable with one or more tracking systems. For example, the patient tracker 58 may include one or more optical trackable members or portions, such as a reflective member 580. It is understood that the optically trackable member may also be an active emitter (e.g. LED) or passive, such as a reflector. Further, the subject tracker 58 may include an electromagnetic tracking member or portion 58e. The EM tracker 58e may be fixed relative to the optical tracker 58o such that the position (including three-dimensional location and/or one or more degree of freedom orientation) is fixed. Accordingly, the patient tracker 58 may be used as a registration or dynamic reference frame relative to the patient 30 using at least two tracking systems, such as the optical localizer 88 and the EM localizer 94.

The subject tracker 58 may also be used for registration and/or calibration of instruments including the instrument 68 with selected fiducial or registration portion 150. The registration portion 150 may include a divot or indent that the instrument 68 may contact to allow the navigation system 20 to determine a distal end or terminal end of the instrument 68 relative to the tracking device 66. As discussed above, the tracking device 66 may also be tracked in more than one tracking system including the optical tracking device 66o and the EM tracking device 66e.

It is understood that the multiple portions of the tracking device 66 may be fixed together in a single unit, similar to the trackable member or assembly 154. Alternatively, or in addition thereto, the two tracking devices, such as the optical tracking device 66o and the EM tracking device 66e, may be fixed relative to one another on the instrument 68. Accordingly, regardless of the configuration, the position of the EM tracking device 66e relative to the optical tracking device 66o is fixed for a selected procedure, such as a procedure on the subject 30.

In addition to the subject tracker 58, additional tracking elements may also be affixed to the patient 30 including individual or separate member trackers 160, including a selected number for example, 3, including 160i, 160ii, and 160iii. Each of the individual trackers 160 may also be referred to as tracking devices and may be fixed to different bony portions that may be movable relative to one another, such as different vertebrae including a first vertebra 166i, second vertebra 166ii, and a third vertebra 166iii. Accordingly, each vertebra of the vertebrae 166 may move relative to one another, such as the first vertebra 166i and the second vertebra 166ii. The individual trackers 160 connected to the individual vertebra may allow for tracking of the individual vertebra relative to one another, as discussed further herein.

Figure 3:
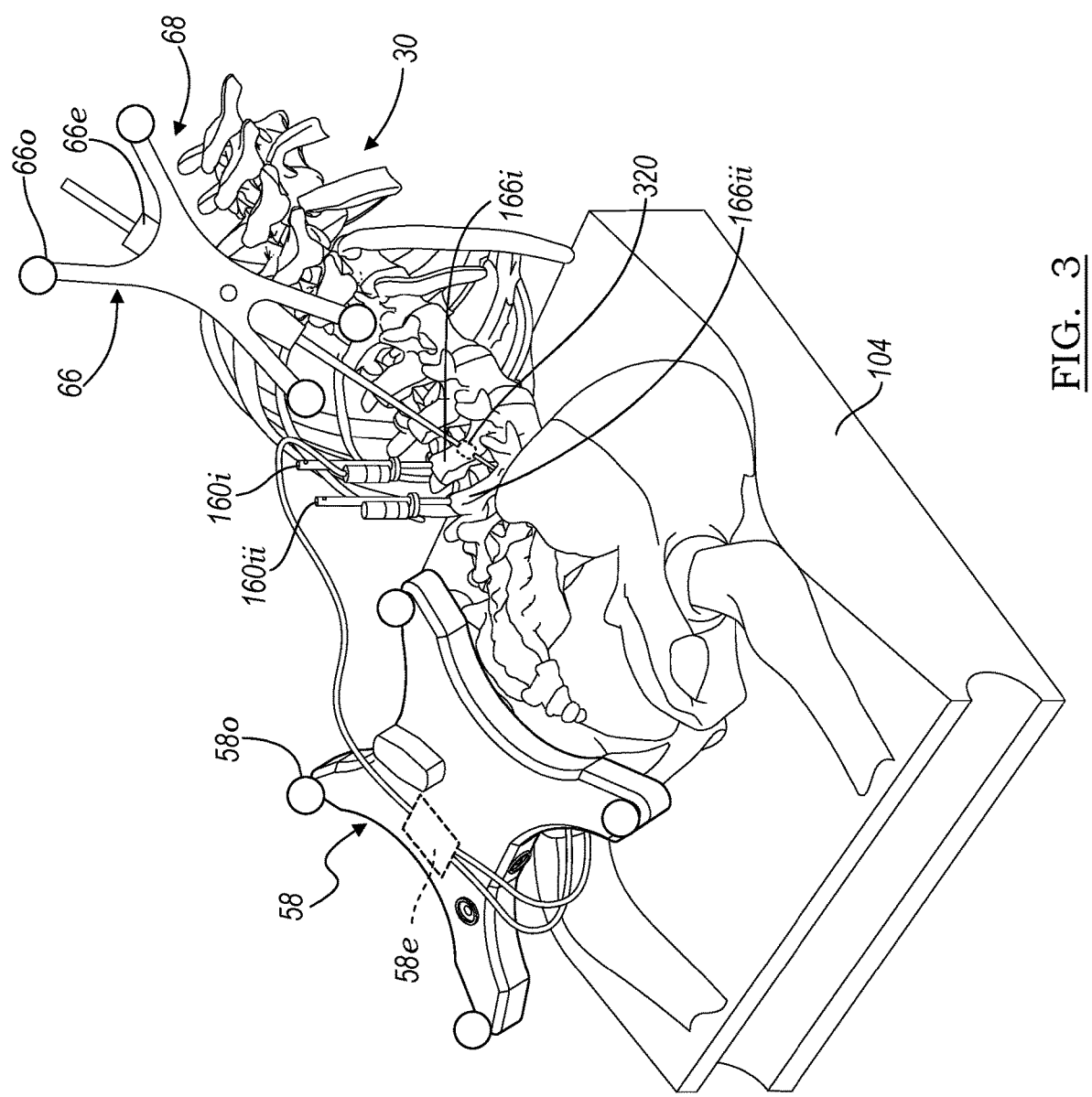
FIG. 3 is a detailed environmental view of a tracking system, according to various embodiments.
Figure 4:
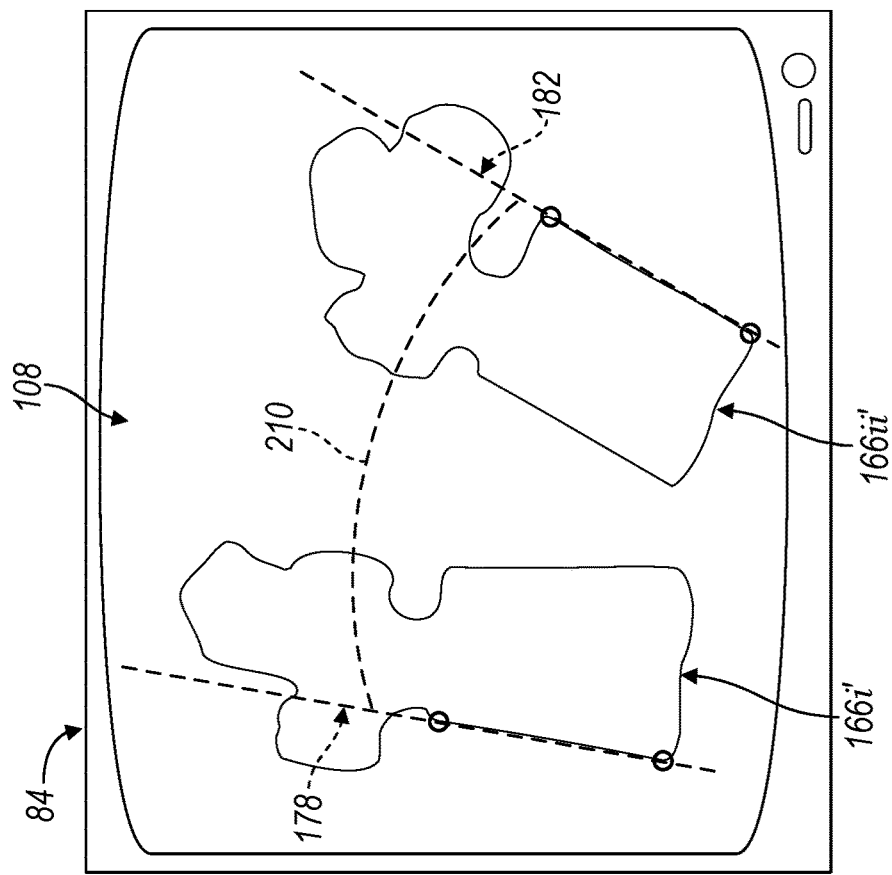
FIG. 4 is a display device illustrating a first image.

With additional reference to FIG. 3 and FIG. 4, the patient tracker 58 may be fixed relative to the subject 30, such as to a portion of the pelvis, including the iliac crest, or other appropriate portions. Further, the subject 30 may be fixed relative to the table 104 and the patient tracker 58 also fixed to the table 104, such that there is not movement between the patient 30 and the patient tracker 58. Regardless, the patient tracker 58 may be used to maintain registration of the subject 30 relative to the image 108 by measuring and tracking movement of the subject 30 to update a translation that between the subject 30 defining the subject space and the patient tracker 58 in the navigation space relative to the image space.

The patient tracker 58, as discussed above, may include the EM tracker 58e. The EM tracker 58e may communicate with the navigation system 20, such as through the controller 110, in an appropriate manner such as a wireless, wired, or combination thereof. Similarly, or in addition thereto, the member trackers 160, such as the tracker 160i may also communicate with the navigation system 20 via a wired communication, wireless communication, or combination thereof. As illustrated in FIG. 2 and FIG. 3, the vertebrae, including the first vertebra 166i and the second vertebra 166ii may each include or have connected thereto a respective tracker or tracking device 160i, 160ii, respectively. Accordingly, each of the tracking devices 160 may track a selected member or element, such as the bony portion including the vertebrae 166.

As discussed above, the tracking system may track the bony portions or the tracking devices connected to the bony portions in real time. The image 108 may include image data or images of the vertebrae, such as the first vertebra 166i' and the second vertebra 166ii'. The vertebrae, include each vertebra, may be segmented in the image in any appropriate manner, such as in a substantially automatic process, manual process, or a combination of manual and automatic processes. The segmentation of the vertebrae may include segmentation such as that used by the Mazor X® Robotic system to segment vertebrae or other appropriate segmentation techniques. A manual segmentation may include the user 72 outlining or defining the portions of the image relating to selected portions, such as the first vertebra 166i and the second vertebra 166ii. An automatic segmentation may include a processor, such as the processor 102, executing an algorithm to segment the vertebrae in the image. A semi-manual segmentation may include the user 72 identifying a seed pixel or voxel or multiple seed pixels or voxels and the processor may execute instructions to segment image data that are related to the identified seed portions. Nevertheless, the image 108 may include segmented portions, such as segmentation of the first, second, and third vertebrae 166.

In addition to segmentation of the vertebrae, various portions thereof may be identified. In various embodiments, superior and inferior endplates of the vertebrae may be segmented or identified in the image 108, such as end plates including a first end plate 170i of the first vertebra and a second end plate 170ii of the second vertebra 166ii. It is understood that each of the vertebrae generally include the two end plates and the discussion of the first and second end plate 170, 174 herein is merely exemplary. Further, other portions of the vertebrae may be identified and/or portions or multiple portions of the endplates may be identified. The end plates may be automatically identified (e.g. based on the segmentation and angles determined therein) or may be based on end plate determinations by the user (e.g. identifying ends of the end plates).

Identification of the end plates 170, 174 may assist in identification of end points or termination portions of the vertebrae 166 in the image 108. Further, planes 178, 182 of the respective first end plate 170 and the second end plate 174 may be identified. Determination or identification of the planes 178, 182 may be used to measure respective distances between the planes 178, 182, such as an anterior distance 184 and a posterior distance 188. The difference in distances 184, 188 may also be used to define or determine an angle 192 between the planes 178, 182. It is further understood that the determination of the angle 192 may be made directly between the plains 178, 182. The planes 178, 182 may also be defined within the boundary of the segmented vertebrae rather than extending therefrom, as illustrated in FIG. 4.

As discussed above the individual or separate tracking devices 160 may be connected to the separate vertebrae 166. Thus, movement of one vertebra, such as the first vertebra 166i relative to the second vertebra 166ii may be tracked using the respective tracking devices 160i and 160ii. The tracked changes may then be illustrated on the display device 84 by altering the image 108, as discussed herein, based upon the tracked positions of the tracking devices 160.

Figure 5:
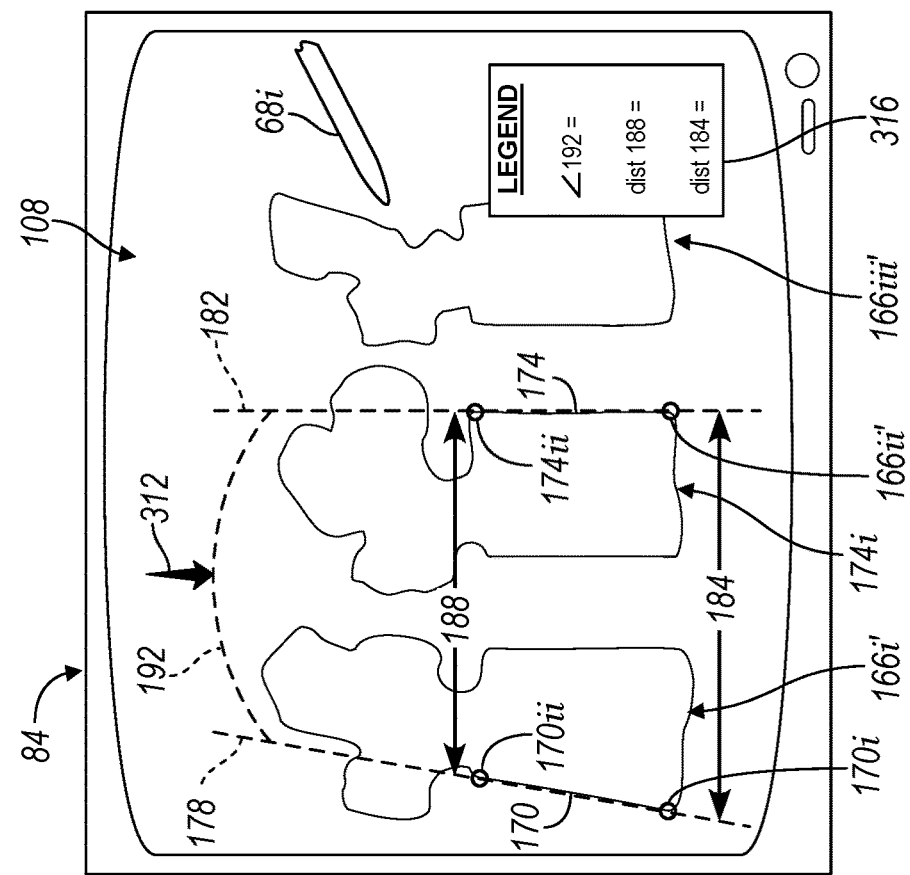
FIG. 5 is a display illustrating a second image.

With reference to FIG. 5, the vertebrae, for example the second vertebra 166*ii* may be moved relative to the first vertebra 166*i* for various purposes, such as attempting to achieve alignment, measuring mobility of the vertebrae, or the like. Accordingly, the display 84 may display the image 108 to illustrate movement of the second vertebra 166*ii* as the image portion 166*ii*'. The end plates 170, 174 and respective planes 178, 182, having been previously identified, may be illustrated and/or measured relative to each other on the display 84. In various embodiments, the user 72 may provide an input, such as enter a command, with the navigation system 20 to determine a measurement after movement of the second vertebrae 166*ii*. Substantially automatically during a procedure, as well, determination of measurements may be made and/or displayed. The navigation system 20, or appropriate system, may measure the distance or angle, such as a second angle 210 between the planes 178, 182. Thus, the user 72 may determine or understand the movement or position between the two vertebrae 166*i* and 166*ii*.

Further, after acquisition of the image data and illustrating the image 108 in positioning the tracking devices 160 in the respective vertebrae 166, the user 72 may also view the position of the vertebrae relative to one another and perform manual manipulation of the vertebrae 166. As discussed further herein, the user 72 may view movement of the vertebrae 166 on the display device 84 without requiring acquisition of additional image data of the subject 30. In various embodiments, therefore, radiation of the subject 30 and/or user 72, or other users relative to the subject 30, may be reduced as the image 108 may be altered based upon the tracked position of the individual vertebrae 166 due to the respective tracking device 160. It is understood, in addition to the vertebrae, other appropriate members and/or instruments may be separately tracked and their positions may be displayed with the display device 84.

Further, as noted above, the subject 30 may be registered to the image 108 in an appropriate manner. Once the subject 30 is registered to the image 108, the subject tracking device 58 may be used to maintain the registration. As discussed above, the subject tracking device 58 may include the EM tracking device and the optical tracking portions 58*o*. Accordingly, the optical localizer 88 and the EM localizer 94 may track the patient tracker 58. Further, as both the EM tracking device 58 and the optical tracking portions 58*o* are fixed relative to the patient 58 at a single location, such as via a connection or clamp 214, both of the localizers 88, 94 of the respective tracking system may include a single origin or relative reference frame for tracking additional elements or portions relative thereto. Accordingly, the instrument 68, as discussed above, may include one or both tracking devices 66*e* and 66*o* to be tracked relative to the subject 30 and have a representation 68*i* illustrated relative to the image 108.

As each of the tracking devices 160, and others as discussed herein, may be connected to the subject, they may also be used to maintain and/or confirm registration. The tracking devices 160 may include a single tracking modality (e.g. optical or EM) while the patient tracker 58 may include multiple tracking modalities (e.g. both optical and EM) to allow for correlation between the two tracking modalities.

It is understood, however, that other tracking devices, such as the subject member tracking device 160 may include only a single tracking modality or type of tracker, such as an EM tracker. According to various embodiments, therefore, the individual member trackers 160 may only include a single type of tracking device. In various embodiments, the EM tracking devices may include one or more members of conductive material formed into coils that may sense and/or emit and electromagnetic field. The coils may be a selected size and configuration to allow for efficient positioning relative to the selected subject members. It is understood, however, that the individual tracking members 160 may also be formed or provided as other appropriate members, as discussed further herein.

Movement of the vertebrae 166, such as the second vertebra 166*ii* relative to the first vertebra 166*i* may be made by any appropriate mechanism. The movement may be, however, illustrated on the display 84, as illustrated in FIG. 4 and FIG. 5, once identification of respective tracking devices relative to the respective vertebrae is made. For example, the user 72 may use the input 106 to identify the first vertebra 166*i* and the tracking device 160*i* associated therewith. Similarly the user 72 may associate the image 166*ii*' with the vertebra 166*ii* and further associate the second tracking device 160*ii* with the vertebra 166*ii*. The user 72, or any appropriate person, may identify the respective tracking devices with the respective vertebra (or any appropriate individual or separate member). Thus, the tracking system and/or tracking systems 88, 94 may track the respective tracking devices individually. The signals from the respective individual tracking devices 160 may then be used to identify the particular portions or members being moved or tracked as moving. The identified specific members are then related to graphical portions of the image, to allow the image 108 to be updated to illustrate movement of the respective member or portions of the subject 30.

The individual tracking devices may also be assigned to the selected members substantially automatically. For example, the patient tracker 58 may be known to be at a selected position, such as on the pelvis. The pelvis may be determined in the image (e.g. by selection or segmentation). The other members, such as the individual vertebra, may be segmented in the image 108. The navigation system may be determined or be instructed with an input that the three vertebra closes to the pelvis have a tracking device connected thereto. The navigation system may, then, determine the vertebra in sequence based on the segmentation and assign to each the tracked tracking devices, in sequence of distance from the patient tracker 58 on the pelvis.

The tracked motion can be substantially in real time, such as a delay of less than one second, including a delay of less than 10 milliseconds between movement of the member portions (e.g. vertebrae 166) and illustration of movement on the display 84 by changing of the image 108. Thus, the user 72 may view the image 108 with the display device 84 to understand substantial real time position and/or movement of the respective members of the subject 30.

Figure 6:
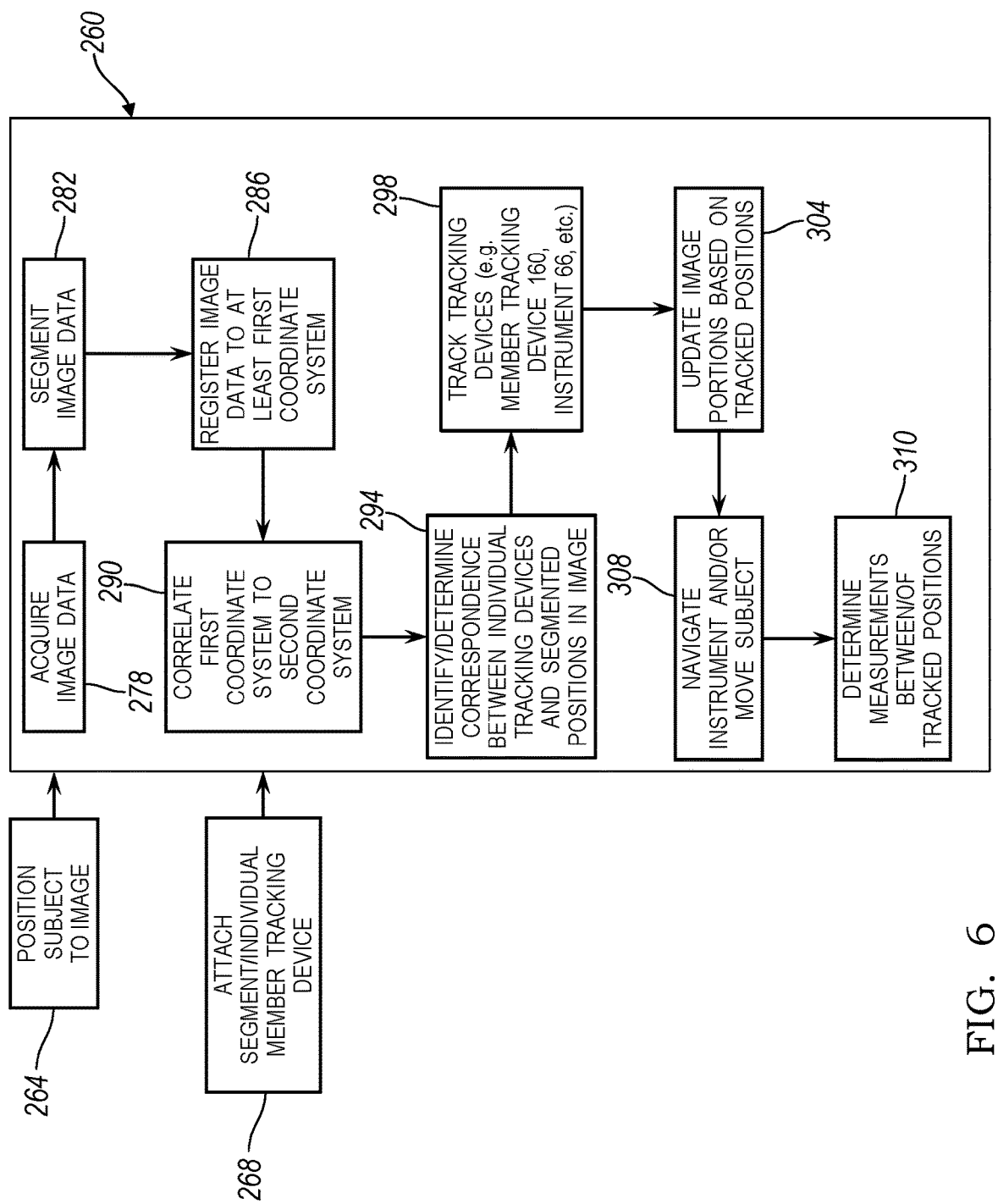
FIG. 6 is a flowchart of a method.

With continuing reference to FIG. 4 and FIG. 5 according to various embodiments, therefore, a procedure relative to the subject 30 may be performed with the navigation system 20. With additional reference to FIG. 6, a method 260 of performing a procedure, according to various embodiments, relative to the subject 30 is illustrated. The method 260 is generally understood to include features or portions that may be executed with input from the user 72, or other appropriate users. Accordingly, according to various embodiments, the subject 30 may be positioned relative to the imaging system 80 at an appropriate time in block 264. It is understood that the subject 30 may be positioned relative to any appropriate imaging system and the imaging system 80 is merely exemplary. Further the individual member tracking devices or segmental member tracking devices 160 may be connected to appropriate members, such as individual vertebra 166 in block 268. These various steps may occur at any appropriate time, including to allow for the method 260 to occur or be performed, as discussed further herein.

The method 260 may include acquisition of image data in block 278. The acquisition of the image data in block 278 may include scanning the subject 30 with the imaging device 80, substantially at a selected time, or any other appropriate imaging device. Further the acquisition of image data in block 278 may be the recall or accessing of image data acquired at an appropriate time, such as prior to positioning the subject 30 in the operating theater relative to the navigation system 20. In various embodiments, therefore, image data may be acquired of the subject 30.

The image data may then be segmented in block 282. Segmentation of the image data may be segmented in any appropriate manner, as discussed above. The segmentation may include segmenting the individual vertebrae 166 in the image, such as the first vertebra image 166i' and the second vertebra image 166ii'. Various segmentation techniques, including those discussed above, may be used to segment the vertebra. Further, if specific or detailed edge extraction or segmentation may not be required, the user 72 and/or the processor system 102 may identify various endpoints, such as endpoints of the end plates 170, 174. Accordingly, for example, as illustrated in FIG. 4, the user 72 may identify two end points 170i and 170ii on the first vertebrae image 166i' and two separate end points 174i and 174ii relative to the second vertebrae image 166ii'. The two points may be used to identify the respective end plates 170, 174 and/or planes 178, 182 and perform various functions and analysis relative thereto. It is understood, however, that the segmentation may be used to automatically determine endplates and/or planes based upon the geometry of the segmented portion, relative portions, etc. Accordingly, segmentation of the image data in block 282 may include segmenting all edges or boundaries of respective portions and/or identifying appropriate or selected portions, such as identifying endpoints and determining lines or planes relative thereto.

Registration of the image data to at least a first coordinate system occurs in block 286. Registration to the image data may be to the acquired image data from block 278 and/or the segmented image data in block 282. Regardless, registration may be made to a first coordinate system, such as the coordinate system of the optical localizer 88. Therefore, the image data may be registered in the first coordinate system which may be defined by the optical localizer 88. It is understood that the first coordinate system may be any appropriate coordinate system, and reference to optical localizer 88 is merely for example.

Nevertheless, once registration to the image data is performed in block 286 a correlation between the first coordinate system and a second coordinate system may occur in block 290. For example, as discussed above, the EM localizer 94 may also be used to define a navigation or tracking space relative to the subject 30. Correlation between the first coordinate system of the optical localizer 88 and the second coordinate system of the EM localizer 94 may be performed due to the patient tracker 58 including both the EM tracking device 58e and the optical tracking device portion 58o. As discussed above, the patient tracker 58 holds both of the EM tracking device 58e and the optical tracking device 58o relative to a single fixed point, also referred to as a reference point. Accordingly, registration of either one of the portions, such as the optical tracking portion 58o to the image data may be then used to correlate the single point to the second coordinate system of the EM tracking system due to the EM tracking device 58e fixed relative to the same point. It is understood, therefore, that additional tracking devices may also be associated with the patient tracker 58. For example, a radar tracking device may also be associated with the patient tracker 58 to allow for correlation to a radar tracking system which may define a third coordinate system.

At an appropriate time, such as after registration of the image data to the first coordinate system and/or correlation between the first coordinate system and the second coordinate system, identification or determination of correspondence between the individual tracking devices and the segmented portions in the image is made in block 294. The identification in block 294 may be understood to allow for an association of a specific segmented portion in the image 108, such as the segmented image portion of the vertebra 166i', to be associated or related to a specific vertebra 166i of the subject. It is understood that any other appropriate association of members may also be made.

As discussed above, the individual portions in the image, such as the individual vertebra 166 may have one tracking device 160 attached thereto. As also discussed above, the individual tracking devices may be tracked in any appropriate tracking system. However, as illustrated in FIG. 2 and FIG. 3, the individual tracking devices 160 may be tracked in a single manner, such as with the EM localizer 94. Other instruments, such as the instrument 68, may be tracked with a different tracking system, such as the optical tracking system 88. Accordingly, the registration of the first coordinate system may be with the optical tracking system, and the second coordinate system may be the EM tracking system. Accordingly, the correlation between the first coordinate system and the second coordinate system may allow for the tracking in the second tracking system to be related to the image data that is registered in block 286. Thus, if the individual tracking devices 160 are tracked relative to the second coordinate system, the identification or determination of correspondence in block 294 may occur after the correlation in block 290.

The identification or determination of the individual tracking devices 160 relative to each of the vertebrae 166 may occur as discussed above. For example, the user 72 may identify each of the tracking devices individually relative to each of the vertebrae images 166i', 166ii' and 166iii'. Thus, the navigation system 20 may identify which of the graphical image portions or segmented portions to relate to each of the individual tracking devices. It is understood, however, that the individual tracking devices may also be automatically related to the individual segmented portions. For example, the patient tracker 58 may be determined or known to be the most inferior trackable portion and that an individual tracking device may be attached to each vertebrae moving superiorly therefrom. Accordingly, the navigation system 20 may identify the patient tracker 58 and then identify, in sequence, each individual tracking device a distance from the patient tracker 58 where the closest tracking device is in the closest vertebra, the next closest tracking device in the next closest vertebra, and so forth. Accordingly, the navigation system 20 may also identify the segmented elements relative to each of the tracking devices substantially automatically in the operating theater.

The individual tracking devices, including the individual tracking devices 160 connected to the member, such as the vertebra 166, the instrument tracking device 66, and other tracking devices are tracked in block 298. Tracking the tracking devices in block 298 may include determining positions of the tracking devices in the navigation space.

Tracking the tracking devices in block 298 allows for determination of positions of portions that are connected to the tracking devices, such as the individual member portions including the vertebrae 166. Accordingly, in block 304 the image 108 may be updated, including the segmented image portions thereof, may be updated based upon the tracked positions of the individual tracking devices. As illustrated in FIG. 4 and FIG. 5, the image portions of the vertebrae 166*i'* and 166*ii'* may be displayed based upon a tracked position of the tracking devices associated thereto. Thus, the tracking devices 160 track the related portions, such as the vertebrae 166, which may be moved and the image portions 166' related thereto may be changed or updated on the image 108 displayed on the display device 64.

The user 72 may then move the vertebrae and/or instruments 68 relative to the subject in block 308. As discussed above, the instrument 68 may include any appropriate instrument such as a tap and/or implant to be positioned relative to the subject 30. The user 72 may move the instrument 68 relative to the subject and the graphical display or icon 68' may be displayed on the display device, as illustrated in FIG. 4 or any appropriate representation of the instrument 68 may be illustrated. Further, movement of the subject 30 may be illustrated on the display device 84 by updating the image 108, as discussed above. In various embodiments, measurement and/or illustration of selected measurements, such as the angle 192, distances 184, 188, or other appropriate measurements may be made in block 310. These measurements may be displayed on the display device 84, such as with graphical block relative to the image 108 including a discrete or small graphic 312 and/or a legend 316. Accordingly, the user 72 may review the various measurements based upon the segmentation of the image 108 and/or movement of the various portions of the subject 30 and/or tracking of the instrument 68.

In various embodiments, as noted above, the members or elements in the navigation field may be tracked with individual trackers connected thereto. Further the portions or members moved relative to the subject 30 may also be tracked with a plurality of tracking devices. As discussed above, the instrument 68 may be tracked relative to the subject 30 with the instrument tracking device 66.

As also discussed above, the instrument 68 may represent a plurality of instruments, such as ones assembled of a plurality of members. In various embodiments, therefore, different portions of the instrument 68 may be connected together and each of the different portions or members may have a tracking device associated therewith. In this regard, with reference to FIG. 3, the instrument 68 may include the instrument tracking device 66 and a second instrument tracking device 320. The second tracking device 320 may be of a type similar to the EM tracking device 66*e*, or be any appropriate tracking device. Nevertheless, the second instrument tracking device 320 may be used to track a portion or member of the instrument 68 spaced apart or away from the connection point of the instrument tracking device 66 to the instrument 68. It is understood, that a plurality of tracking devices may also be associated with various other members, such as implants, particularly movable or adjustable implants that may have portions that move relative to one another either intentionally or unintentionally.

Figure 7:
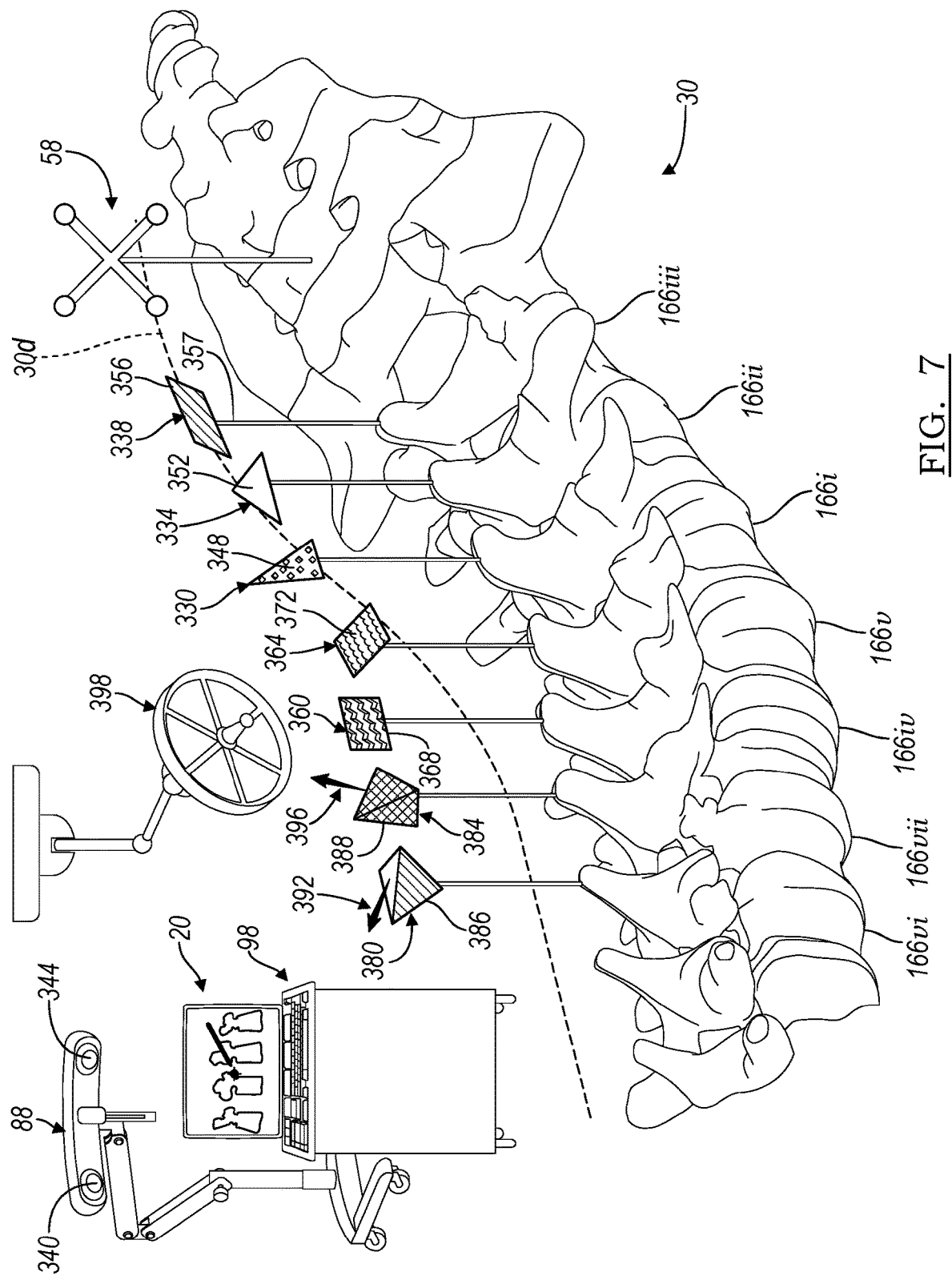
FIG. 7 is a detailed environmental view of a tracking system, according to various embodiments.

Turning reference to FIG. 7, the patient tracker 58 may be connected to the subject 30 in a selected location, such as near the tail bone or iliac crest. The other trackers may be connected relative to the subject 30 at other appropriate locations, such as to the vertebrae 166. The vertebrae 166 may have distinct and separate tracking devices connected thereto, as may be provided in various embodiments. As discussed herein, each of the various tracking devices may vary in size, geometry, shape, color, tracking modality, etc.

In various embodiments, as illustrated in FIG. 7, tracking devices are illustrated that may be provided or used in addition to or alternatively to the tracking devices 160. For example, a first tracking device 330 may be connected to the first vertebrae 166*i*, a second tracking device 334 is connected to the second vertebrae 166*ii* and a third tracking device 338 may be connected to the third vertebrae 166*iii*. Each of the tracking devices 330, 334, 338 may be within a field of view or navigation space of the optical localizer 88. The optical localizer 88 may include a plurality of cameras, such as a first camera 340 and a second camera 344. The cameras 340, 344 may view the field of view that may define all or a portion of the navigation space. The navigation system 20, therefore, may view the field of view or analyze the field of view to identify the individual tracking devices 330-338.

Each of the tracking devices 330-338 may include distinct shapes or geometry, such as triangles or other geometric shapes that are different from one another. For example, the first tracking device 330 may have a tracking element or member 348 that is an acute triangle. The second tracking device 334 may have a trackable element 352 that is an obtuse triangle. Finally, the third tracking device 338 may include a trackable element 356 that is a parallelogram. Each of the trackable elements 348, 352, 356 may, therefore, be identified in the field of view by the navigation system 20. As discussed above, each of the trackable devices 330-338 may be associated with respective vertebrae 166. Therefore, the navigation system may track the tracking devices 330-338, substantially separately and individually, and relate or alter the display device 84 to display the image 108 regarding a substantially real time position of the respective vertebrae 166, or the member to which the respective tracking devices are connected. In addition to the altered shape or different shape of each of the tracking portions 348-356, each may include a different color, shade, or the like that may also be identifiable in the field of view. Accordingly, each of the individual tracking devices may be identified by both a shape and/or color during a selected tracking procedure.

With continuing reference to FIG. 7, tracking devices may also include or alternatively include a fourth tracking device 360 and a fifth tracking device 364. Each of the tracking devices 360, 364 may be connected to selected individual vertebrae or members, such as a fourth vertebra 166*iv* and a fifth vertebra 166*v*. It is also understood that the tracking devices 360, 364 may be used in place of alternatively to the tracking devices 330, 334, 356 or other appropriate tracking devices as discussed above.

The tracking device 360, 364 may include respective trackable elements or members 368 and 372. The trackable element 368 may include a first pattern or light altering characteristic that may be known. For example, the navigation system 20 may include a database that includes the pattern of the trackable portion 368. In addition the trackable portions 348, 352, 356, as discussed above, may also be included in the database. The second trackable portions 372 may include a different pattern or light changing characteristic. Selected camera or lens features, such as a plenoptic camera or when using a structured light emitter, may be used to identify the differentiation of the light reflected from the trackable portions 368, 372. The trackable portions 368, 372 may include a three-dimensional pattern formed on to the trackable portions 368, 372 that may alter light emitted therefrom or reflected thereby. The selected camera 340, 344 may be used to identify the type of reflected light and identify the specific tracking members 360, 364. For example, a plenoptic camera may include a plurality of lenses positioned away from a focus plane to analyze light encountering a photo cell or light receiver (e.g. a complementary metal-oxide semiconductor sensor). By analyzing the reflected light the navigation system 20 may be able to identify the specific tracking device 360, 364. As discussed above, each of the individual tracking devices may be associated with individual vertebrae, such as the fourth and fifth vertebrae 166iv and 166v. Thus the navigation system 20 may identify the specific vertebrae and update the image 108 based upon the tracked position of the tracking devices 360, 364.

With continuing reference to FIG. 7, still further or alternative tracking devices may include a tracking device 380 and a tracking device 384. Each of the tracking devices 380, 384 may have trackable portions 386, 388, respectively. Each of the trackable portions 386, 388 may be substantially three-dimensional or have depth to alter or change the direction of light being reflected. Thus, each of the trackable portions 386, 388 may be identified based upon the direction or altered or predicted type of reflected light. For example, the trackable portion 386 may reflect light from a source along a first ray 392. The second trackable portion 388 may reflect light along a second ray 396. As the two rays represent, the trackable portions may reflect light in different directions. The light may be from a single source 398 and the cameras 340, 344 of the localizer 88 may identify the specific light reflection to identify the respective tracking device 380, 384. As discussed above, the various portions of the trackable portions 386, 388 may also be altered or differentiated by color, reflection features, or the like.

Thus, the respective and individual tracking devices 380, 384 that may be connected to different and separate vertebrae 166vi and 166vii may be used to identify the respective vertebrae during a tracking procedure. As discussed above, the navigation system 20 may then update the image 108 to identify movement of position of the respective members of the subject 30, such as the vertebrae 166. The updated image may be based upon the tracked location of the respective and individual tracking devices 380, 384.

It is understood that appropriate types of tracking devices may be associated with a vertebrae 166 in any appropriate manner and may include electromagnetic or convective coils (EM) that may be used to sense a field and transmit a signal thereon. Identification of the individual tracking devices may include a signal regarding each of the individual tracking devices. In a wired transmission, the individual signal may relate to the specific tracking device transmitted with a wire or physical connection. In a wireless transmission system, selected identification features may be added to the transmitted signal to identify the specific tracking device transmitting the signal. Examples include a tracking device serial number or a hard-coded universally unique identifier (UUID). Other possible tracking devices may also include radar tracking devices, radio frequency tracking devices, ultrasonic tracking devices, or the like.

In addition to tracking each of the respective vertebrae relative to a selected reference, such as the patient tracker 58, each of the respective tracking device may be used as reference markers for tracking other elements relative to them. For example, the first tracking device 330 may be tracked relative to the second tracking device 334, once both are registered within the navigation coordinate system. As discussed above, the patient tracker 58 may be registered to the image 108 and may include a plurality of trackers such that the selected type of tracker of the tracking devices connected to the individual, including those illustrated in FIG. 7 and those discussed above may be tracked relative to the patient tracking device 58 and/or other tracking devices in the navigation field.

In various embodiments, a plurality of types of trackers may be divided as the tracking devices associated relative to the subject 30 for assisting in tracking a plurality of types of procedures. As illustrated in FIG. 7 and in the FIGS. above, trackable portions may be connected to members that are fixed directly to bony portions, such as the vertebrae. Each of the tracking devices may include pins, screws, or the like that are fixed to the bony portions and the tracking devices may extend through soft tissue of the subject, such as a dermis or muscle thereof. As illustrated in FIG. 7 and phantom, therefore, a dermal layer 30d may cover a portion of the vertebrae 166 such that the trackable portion 358 extends past the dermis and a pin or connection member 367 extends into the vertebrae 166iii. It is understood that the other tracking devices may include a similar connection mechanism such that the trackable portions extend above the dermal layer 30d. In various embodiments, however, the trackable portions of the tracking devices may be connected to the vertebrae and alternative and/or additional manners.

Figure 8:
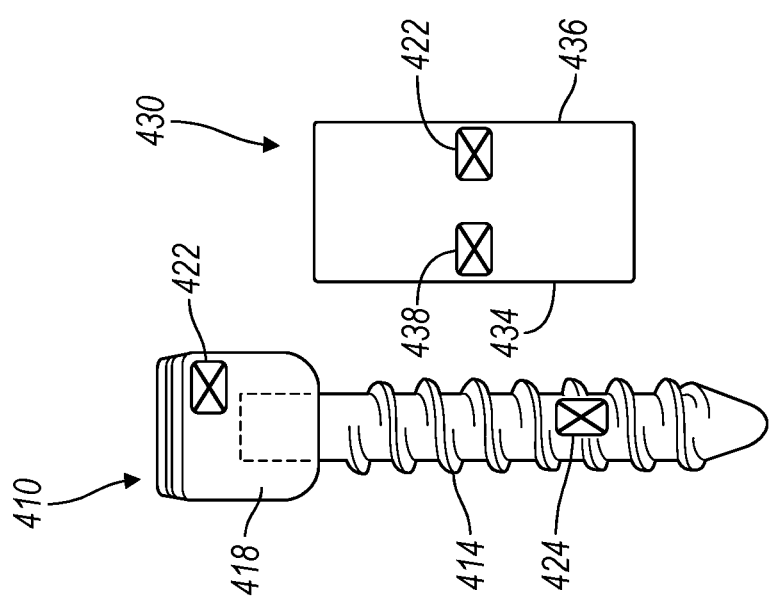
FIG. 8 is an illustration of instruments with tracking devices, according to various embodiments.

In various embodiments, as illustrated in FIG. 8, implants may be positioned relative to the subject 30. As discussed above, the implant is the instrument 68. In various embodiments, however, an implant may include a fastener, such as a pedicle screw 410. The pedicle screw may include various portions, such as a shank 414 and a head 418. The pedicle screw 410 may be any appropriate pedicle screw such as a pedicle screw sold with the CD Horizon® Spinal System sold by Medtronic, Inc. having a place of business in Minnesota, USA. The pedicle screw may allow the head 418 to move relative to the shank 414.

The pedicle screw 410 may include tracking members, such as a first or head tracking member 422 and a second or shank tracking member 424. The tracking members may be tracked by the tracking system in the navigation system 20. In various embodiments the tracking members 422, 424 may be EM tracking members.

Other trackable devices may include an intervertebral device such as a Prestige® disc replacement or disc implant and/or a Bryan® disc replacement or disc implant, both sold by Medtronic, Inc. An intervertebral device 430 may be positioned between two vertebrae, such as to be positioned between and/or in contact with the end plates 170, 174, as discussed above. It is understood that various intervertebral implants may include surgical implants, lumbar implants, or the like. Generally the intervertebral implant 430 may include a first end plate or contact side 434 and a second implant or contact side 436. Positioned near or adjacent to the two sides 434, 436 may be tracking devices such as a first tracking device 438 and a second tracking device 442. Again, the tracking devices 438, 442 may be EM tracking devices to be tracked with the navigation system 20.

In either instance the tracking devices 422, 424, 438, 442 may be used to track the position or relative position of different portions of the respective members 410, 430. For example the two tracking devices 422, 424 may be used to track the relative position of the head 418 to the shaft 414. The tracking devices 438, 442 of the intervertebral implant 430 may be used to show the distance between the two surfaces 434, 436 or relative angles thereof, or the like.

Further, the tracking devices associated with the implants 410, 430 may be used during a procedure. For example, the pedicle screw 410 may be positioned into a vertebrae, such as the vertebrae 166*i*. The tracking devices in the screw 410 may be used to track the screw as it is positioned within the vertebrae 166*i*. Once the screw 410 is positioned within the vertebrae 166*i* the tracking devices or a selected one of the tracking devices on the screw 410 may then be used as the tracking device for the particular vertebrae, in addition to or alternative to the tracking devices (e.g. 160 as discussed above) as discussed above. Similarly the tracking devices 438, 442 of the intervertebral device 430 may be used to track the intervertebral device 430 that is positioned and then tracked relative to the vertebrae once positioned. It is understood that other appropriate implants may also include tracking devices and may also be used as individual member tracking devices once positioned in the subject.

Figure 9:
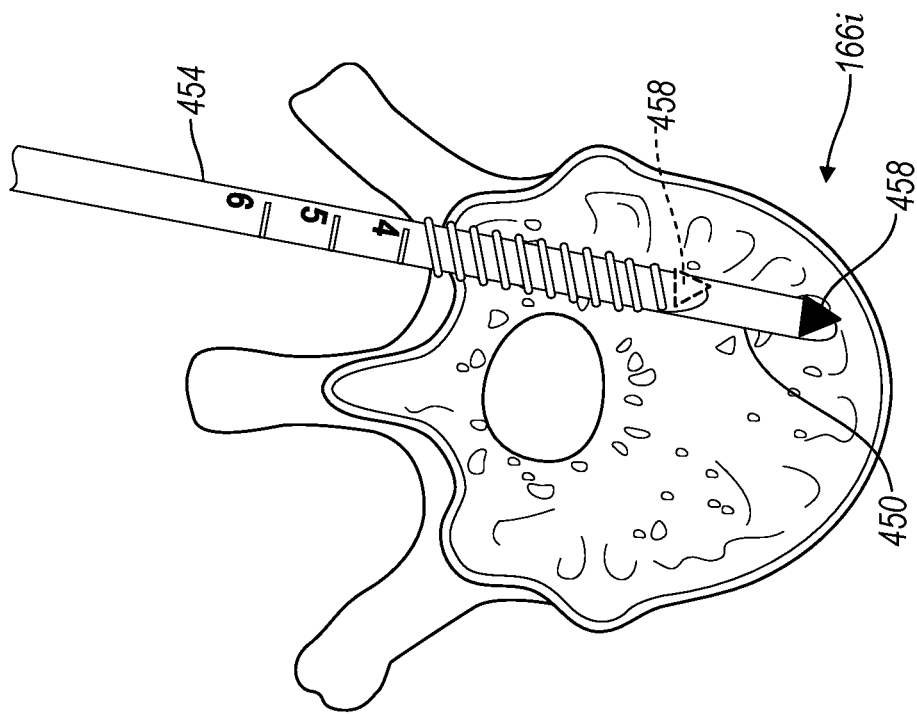
FIG. 9 is an illustration of an instruments with a tracking device, according to various embodiments.

Turning reference to FIG. 9 the vertebrae 166*i* is illustrated. In various embodiments, as discussed above, a pilot bore or a hole 450 may be formed into the vertebrae 166*i* for various purposes, such as positioning the pedicle screw 410 therein. A drill instrument or drill bit 454 may be used to form the bore 450. The drill instrument 454 may be formed to include a trackable portion 458 to track the drill during forming the bore 450. After forming the bore 450, the trackable portion 458 may be disengaged or removed from the drill bit 454 and remain in the bore 450. Accordingly, the tracking device 458 may remain in the bore 450 for a selected portion of a procedure and/or after implantation of other members. In various embodiments, the tracking device 458 is a tracking device tracked by the EM localizer 94. The tracking device 458 may include one or more coils of conductive material.

The trackable portion 458 that disengages from the drill bit 454 may be used as the tracking device to track the individual vertebrae 166*i*. It is understood that other appropriate instruments may be used to perform a first portion of a procedure on a selected member and the drill bit and the vertebrae are merely exemplary. Nevertheless, a tracking portion included in the first instrument portion may be disengaged and remain in the selected member, such as the vertebrae, for further portions of a procedure. The remaining tracking portion may be used as the tracking device for the additional portions of a procedure either alone or in addition to the other tracking devices that may be connected externally to the vertebrae or other member.

It is understood that other appropriate members may also include tracking portions that may either be used to track the instrument relative to the subject 30 and/or particular members thereof such as the vertebrae 166, or other implants. For example, retractors, taps, awls, and the like may engage selected portions of the anatomy either temporarily or during an extended period during a procedure. The tracked portions may be identified with respective portions of the anatomy and may be used to track the specific portions of the subject during the selected portion of the procedure. By tracking the individual portions during the procedure, the image 108 may be updated to illustrate the tracked real time position of the selected member to which the tracking device is connected or associated with.

Figure 10:
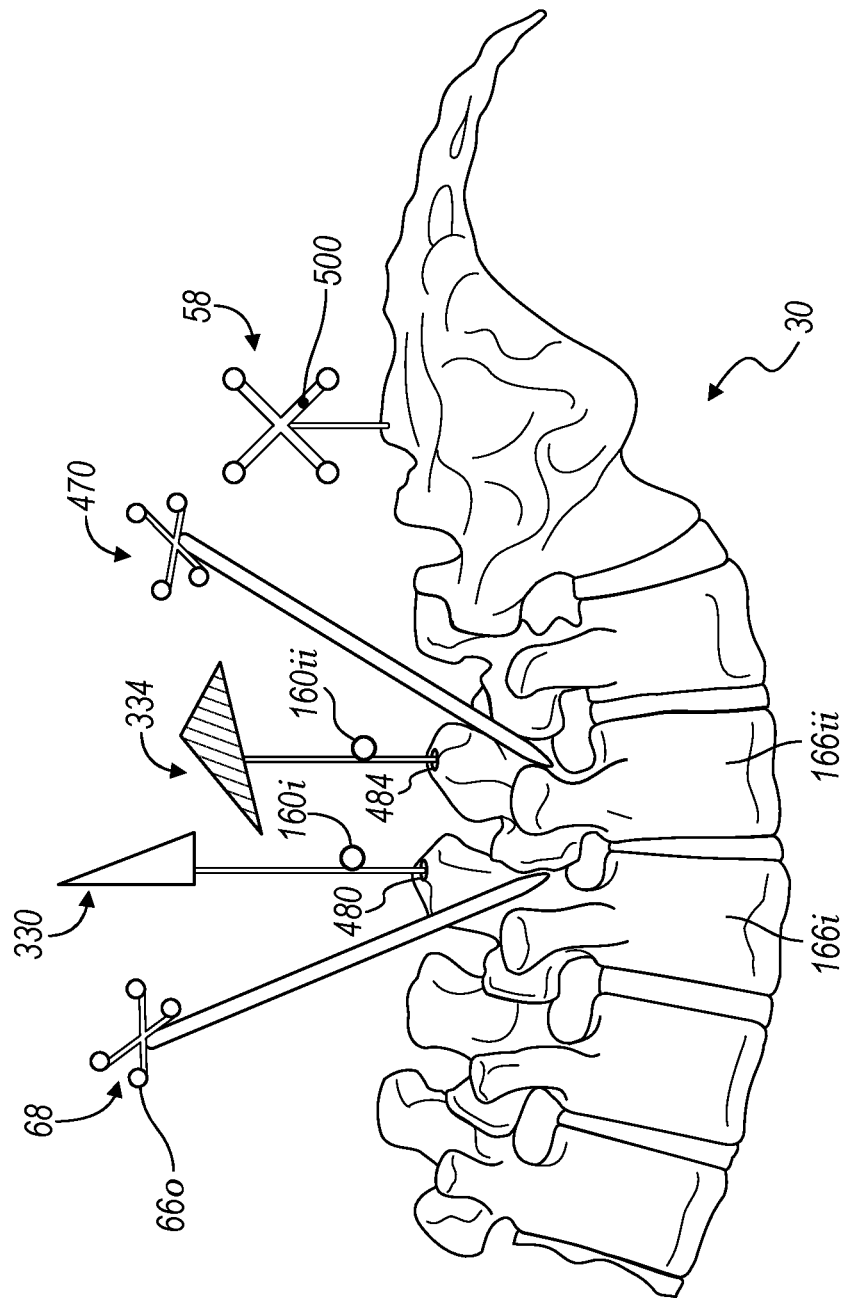
FIG. 10 is a detailed environmental view of a tracking system, according to various embodiments.

Turning reference to FIG. 10, as discussed above, one or more elements or portions, such as bony members including vertebrae, may have a tracking device associated therewith. The tracking device may also be used as the patient tracker or reference frame for tracking relative thereto with another instrument. As discussed above the instrument 68 may be moved relative to the subject 30 during a selected procedure.

As illustrated in FIG. 10 and with reference to FIG. 1 and FIG. 3, the first tracking device 160*i* may be connected to the first vertebrae 166*i* and a second tracking device 160*ii* may be connected to the second vertebrae 166*ii*. The instrument 68 may be tracked relative to the subject 30 during a selected procedure. As illustrated in FIG. 10, the instrument 68 may be movable relative to the subject 10, such as being positioned near the first vertebrae 166*i*. When positioned near the first vertebrae 166*i* the nearest tracking device 160*i* may be used as a reference frame for tracking the instrument 68 relative to the first vertebrae 166*i*. The instrument 68 and/or a separate instrument, such as an instrument 470 may be positioned near the second vertebrae 166*ii*. The instrument 470 may be identical or different than the first instrument 68. Nevertheless, the second tracking device 160*ii* may be the tracking device nearest to the instrument 470 and, therefore, may be used as a reference frame to track the instrument 470 relative to the second vertebrae 166*i*.

It is understood, however, in various embodiments, that only the single instrument 68 may be tracked for a selected portion of a procedure or for a procedure and may be moved between the first vertebrae 166*i* and the second vertebrae 166*ii*. Accordingly, the selection of the tracking device to use as the reference frame may be based upon the determination of the tracking device closest to the instrument 68 during a portion of a procedure. The closest tracking device selected for reference may increase accuracy of tracking the instrument relative to a selected member, such as the vertebra 166.

In various embodiments the single patient tracker 58 may be used as a reference frame. Providing the individual tracking devices 160 on the individual portions allow for each of the individual tracking devices to be used as reference devices once they are registered in the navigation space, as discussed above. Accordingly, the selection of the reference device may be switched between the patient tracker 58, the first tracking device 160*i*, the second tracking device 160*ii*, or other appropriate tracking devices.

In addition to and/or alternatively to selecting the nearest tracking device to the instrument being tracked, a selection of an assumed fixed tracking device may be made based upon the highest quality of measurement. Accordingly, with continuing reference to FIG. 10 and tracking the instrument 68, either the first tracking device 160*i*, the second tracking device 160*ii*, or the patient tracker 58 may be used as the reference tracking device for tracking the instrument 68. The selection of the tracking device for reference in tracking of the instrument 68 may be based upon a quality of the tracking of the selected tracking device connected to the subject 30. The quality of the tracking may be based upon an error in geometry, signal strength, or the like. For example, as discussed above, the tracking device 160*i* may be provided as any appropriate tracking device such as the tracking devices 330, 334, 338. Each of the tracking devices have known geometries that may be used to identify the tracking devices in the navigation space. A lowest error of geometry may be used to determine the tracking devices to be best used as a reference for tracking the instrument 68 relative to the subject 30. Additionally, determination of interference with a signal (e.g. eddy EM fields) may be used to determine the tracking device as the selected reference device.

In various embodiments, a greater confidence or quality may be made based on the tracking device with the least error, including geometry error. Error may be measured as an average or root-mean-square of the differences in measured vs. expected tracking device positions. For example, in an EM tracking device the coils are at known and fixed positions relative to one another. Thus, each coil may be tracked and the entire information may be used to determine the position of the tracking device. However, each coil position may be tracked relative to each other and thus, the known and tracked positions may be used to determine quality of the tracking information. Noise or spurious spectral components could also be used to weight a measurement by signal quality or the presence of interference. Measured signal phases may be also used to evaluating single quality.

Thus, providing a plurality of the tracking devices, such as the first tracking device 160*i* and the second tracking device 160*ii*, in the subject 30 allows for an ability to select different tracking devices for referencing tracking of the instrument 68 relative thereto. The selection may be made substantially automatically and/or manually (e.g. by a user) during a selected procedure. For example the navigation system 20 may receive the tracking signal for each of the tracking devices during a selected procedure. As the instrument 68 is tracked relative to the subject 30 the navigation system 20 may determine a lowest error relative to a plurality of tracking devices connected to the subject 30. Error may be determined by comparing measured vs. expected fiducial properties, including physical dimensions and geometry, color, texture, signal spectral composition and phase, etc. A tracking system 20, therefore, may automatically select the tracking device with the lowest error for navigating or tracking the instrument 68 relative to the subject 30. Similarly the tracking system 20 may measure the distance between the instrument 68 and other tracking devices in the navigation space and select the tracking device closest to the instrument 68 as the tracking device for referencing tracking the instrument 68. Alternatively and/or in combination therewith, the user 72 may select and/or validate or confirm selection of tracking devices for navigating the instrument 68.

With continuing reference to FIG. 10 and further reference to FIG. 7, discussed above, a plurality of tracking devices may be connected to each of the portions of the subject 30. For example, as illustrated in FIG. 10, the vertebrae 166*i* may be connected to the first tracking device 160*i* and the tracking device 330. Similarly, the second vertebrae 166*ii* may be connected to the tracking device 160*ii* and the tracking device 334. Each of the respective tracking devices may be connected at the same point, such as a tracking device or reference point 480 on the first vertebrae 166*i* and a second tracking or reference point 484 on the second vertebrae 166*ii*. Accordingly, the two tracking devices 330 and 160*i* are connected at the single tracking point 480. Similarly the two tracking devices 334 and 160*ii* are connected at the second tracking point 484.

The two different tracking devices may be tracked in different tracking modalities, such as the EM tracking devices 160*i* and 160*ii* and the second tracking portion may be optical tracking device portions 330, 334. Thus, two different tracking systems, including the optical localizer 88 and the EM localizer 94 may be used to track the same points 480, 484. It is understood that a plurality of a type of tracking devices may be connected together and that the same tracking points, such as including radar tracking devices, acoustic tracking devices, and the like. The instruments, such as the instrument 68, may include only one or a plurality of the tracking device modalities relative thereto. Regardless the navigation system 20 may be co-registered relative to the selected portions, such as the individual vertebrae 166 due to the plurality types of tracking devices at the single or tracking points 480, 484.

It is understood that each of the vertebrae or each appropriate member or portion of the subject may have the tracking devices connected thereto. Accordingly during a procedure, the selection of the best tracking device for reference may also be made based upon the tracking system having the greatest confidence of tracking data regarding the reference device. The greatest confidence may be based upon a comparison of confidence levels of tracked positions of various different tracking devices. Confidence may be based on geometric error of the tracking portions alone and/or relative to each other, predicted light (visible or invisible (e.g. infra-red) shaped or diffraction, signal strength or signal to noise ratio, or other considerations. The confidence for each tracking device may be determined at a selected rate during a procedure and used for various purposes, as discussed herein.

During navigation of the instrument 68, the instrument 68 may be tracked with an optical system that tracks the optical tracking device 66*o* while the vertebrae 166*i* is tracked with the EM tracking device such as the tracking device 160*i*. The two tracking systems may be co-registered or correlated due to the prior registration of the tracking device relative to the vertebrae 166*i* either individually and/or with the patient tracker 58. The EM localizer 94 may be used to track the vertebrae 166*i* with the EM tracking device 160*i* and the optical tracking system with the localizer 88 may track the instrument 68 with the optical tracking device portion 66*o*. The position of the vertebrae 166*i* and the position of the instrument 68 may be illustrated as a graphical representation, either superimposed on or by altering the segmented image 108, discussed above.

The multiple tracking portions of the tracking devices allow the tracking of the instrument 68 relative to the vertebrae 166*i* based upon one or a plurality of tracking devices in the navigation system 20. It is understood that a plurality of instruments may also be tracked and that the specific type of tracking system may be selected upon the user 78 or other appropriate selections and the above is merely exemplary. Nevertheless, the vertebrae 166*i* may be tracked with a first tracking modality (e.g. EM tracking) and the instrument 68 may be tracked with a second tracking modality (e.g. optical tracking). The two tracking systems may be co-registered, as discussed above, and allow for illustration of the respective positions of the vertebrae 166*i* and the instrument 68 to be displayed on the display device 84, as discussed above.

The correlation of the tracking systems may allow the tracking device portion 66*o* to be tracked by the optical tracking system relative to the vertebra 166*i* tracked with the tracking device 160*i* which may be an electromagnetic tracking device tracked by the EM localizer 94. Although the two tracking systems may include different localizers operating under different modalities (e.g. optical and different from electromagnetic), the tracked position of the instrument 68 relative to the vertebrae 166*i* may be known due to the correlation between the EM tracking system and the optical tracking system and related coordinate systems. The relation can be due to the tracking device connected to the single point 480 on the vertebrae 166*i* including both the tracking device 160*i* which may be an EM tracking device and the tracking device 330 which may be an optical system tracking device. Additionally, the tracking device 58, discussed above, may include both EM and optical tracking portions which allow for co-registration or correlation between the two tracking systems. The correlation may be made at any appropriate time, such as initially, or during a procedure. The correlation may be made where the two tracking systems (or any appropriate number of tracking systems) may track or determine a single position to allow for correlation between the coordinate systems of all the tracking systems.

As discussed above, the instrument 68 includes the tracking device 66 that may include one or more tracking portions, such as an optical tracking portion 66o and an EM tracking portion 66e. Accordingly, the instrument 68 may be tracked with both of the localizers 88, 94 substantially simultaneously. The two localizers having the two respective coordinate systems may be correlated, as discussed above.

Tracking the instrument 68 in the two coordinate systems may be used to assist in increasing confidence of a tracked position of the instrument 68. The tracked position of the instrument 68 may be tracked with the two tracking systems and the tracked location may be confirmed and/or increased in confidence by tracking with the two tracking systems and/or selecting the tracking system with the least amount of error. Further, the instrument 68 may be tracked substantially continuously, therefore, regardless of interference with either one of the tracking systems. In addition, moving the instrument 68 through space and maintaining tracking it with the two tracking systems may allow for determination of possible interference in different areas of space to either or both of the tracking systems. It is understood that any appropriate number of tracking systems may simultaneously track the instrument 68, and the two tracking systems is merely exemplary.

In addition, the tracking information may be combined from the two or more tracking systems in various approaches. In various embodiments, combining the tracking information may include a sensor fusion approach by applying a central limit theorem or Kalman filtering to the tracking data to determine a tracked position of the instrument 68. Regardless, the tracked position of the instrument 68, or any appropriate portion to which two or more tracking portions allow two or more tracking systems to tracked, may be tracked substantially simultaneously with two or more tracking systems to attempt to increase the confidence and/or precision of a tracked position to which the tracking device is connected.

Further, the instrument 68 may be localized within the tracking coordinate system by positioning it relative to a known point, such as the patient tracker 58. The patient tracker 58 may include a reference point or portion 500, similar to the reference point 150, that may be contacted by the instrument 68. Once the instrument 68 contacts the point 500 the respective tracking systems may register or coordinate the instrument 68 within the navigation spaces. For example, if the patient tracker 58 includes both optical and EM tracking systems the correlation between the tracking systems may be determined and once the instrument 68 touches the instrument portion at point 500. Even if the position of the instrument 68 is tracked with the optical tracking system, with the optical tracking portion 66o only, the correlation allows the instrument 68 to be tracked in the optical tracking system with the optical localizer 88 and to correlated to the EM coordinate system.

Further, the tracking devices on the instrument 68 may be registered or determined by positioning or contacting the instrument 68 with the point 500. The patient reference 58 may be determined in the navigation space and the tracked position of the tracking portion, such as the optical tracking portion 66o may be determined relative to the reference point 500 once the instrument 68 contacts the reference point 500. This may allow the determination of the tracking portion 66o position relative to a selected portion of the instrument 68, such as a distal or terminal point thereof. It is understand that the determination of tracking portions in any appropriate member may be performed in a similar manner or by contacting any appropriate reference point, such as an implant (e.g. a pedicle screw). As an alternative, or in addition thereto, the tracking device 66o, or any appropriate tracking device, may be manufactured or mounted to the instrument 68 at a known or predetermined position. The navigation system 20 may then recall the known and predetermined position to determine a point of the instrument or portions or geometry of the instrument relative to the tracking portion 66o.

Positions of various tracking devices may also be determined relative to the members of the subject 30, such as the tracking device 160i by imaging the subject 30 and identifying the tracking portion in the image. The tracking portion may be identified in the image automatically (e.g. by segmentation of a known geometry), semi-automatically (e.g. user selecting a selected pixel or voxel in a segmentation based thereon), or by a manual selection by the user. Regardless, the identification of the location of the tracking portion 160i (or any appropriate tracking device) may be determined in the image. Thus, when updating the image 108 the known position of the tracking device may be used to assist in determining an appropriate position (e.g. three-dimensional position and appropriate number of degrees of freedom of orientation) in the image.

Figure 11A:
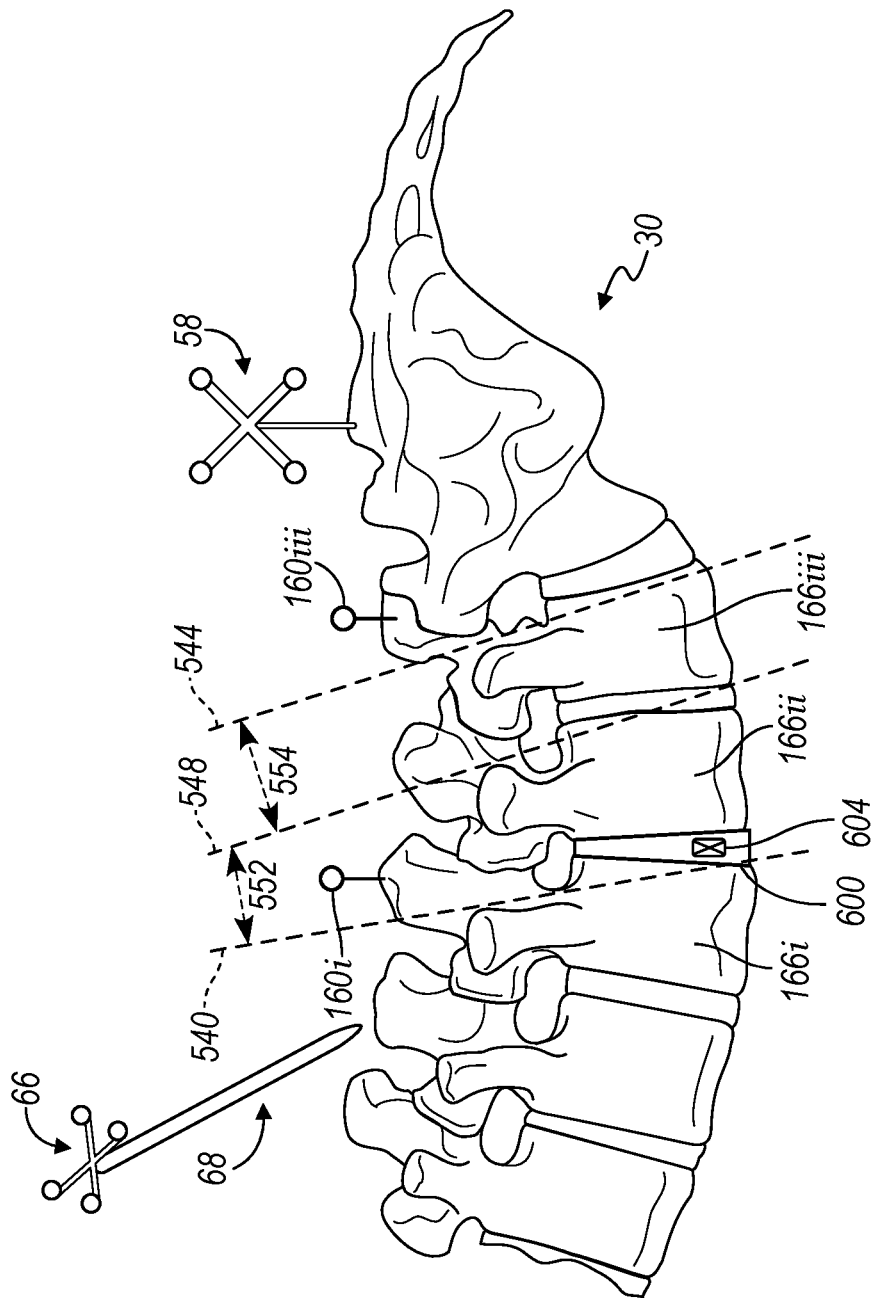
FIG. 11A is a detailed environmental view of a tracking system, according to various embodiments.

Turning reference to FIG. 11, the subject 30 may include a plurality of portions, such as the plurality of vertebrae 166 that may be of interest for a selected procedure. During the selected procedure various tracking devices, such as the patient tracker 58 may be connected relative to the subject 30 along with other appropriate tracking devices such as a third tracking device portion 160iii and a first tracking device portion 160i. As illustrated in FIG. 11A, the first tracking device portion 160i is connected to the first vertebrae 166i. The third tracking device 160iii is connected to the third vertebrae 166iii. The second vertebrae 166ii, however, may have no tracking device connected thereto. As discussed above, the identification of the selected portions of the subject 30 to which tracking devices are connected may be performed in various manners, such as through automatic identification, manual identification, or the like. Nevertheless, the navigation system 20 may illustrate directly the position of the first vertebrae 166i and the position of the third vertebrae 166iii either alone or relative to other portions of the anatomy in the image 108. As discussed above, tracking the movement or position of the respective tracking devices, 160i and 160ii, may allow for direct determination of current or tracked positions of the respective vertebrae to which they are attached.

Figure 11B:
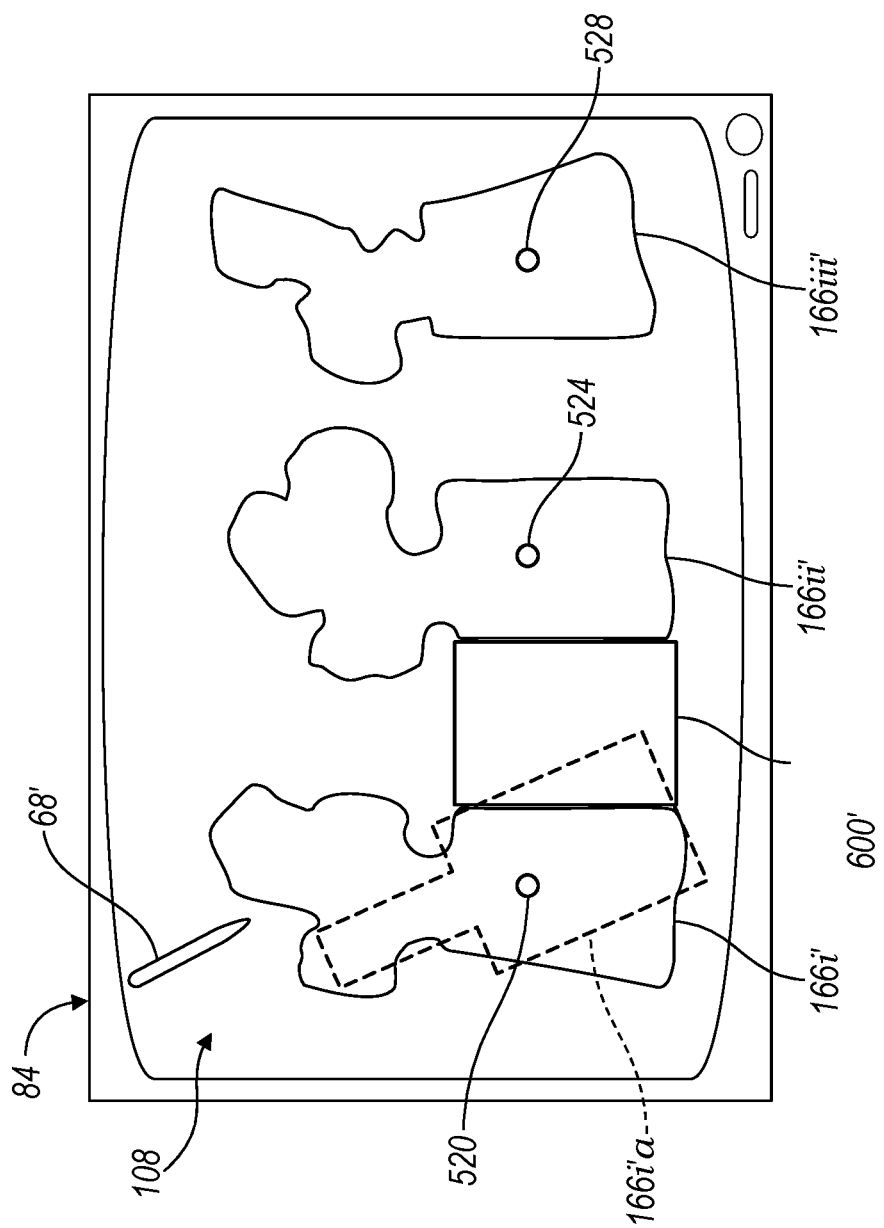
FIG. 11B is a display illustrating an image with tracked portions therein, according to various embodiments.

The second vertebrae 166ii, however, may also be indirectly tracked or have its position estimated relative to either or both of the first vertebrae 166i and the second vertebrae 166iii. For example, the image 108, as illustrated in FIG. 11B all of the vertebrae as images including segmented portions of the vertebrae and/or graphical representations thereof. Thus, the first vertebrae is illustrated as the first vertebrae image portion 166i', the second 166ii', and the third vertebrae 166iii'. As the tracking devices are associated with the different vertebrae, the navigation system 20 may measure a distance between selected portions, such as a centroid 520 of the first vertebrae image 166i', a second centroid 524 of the second vertebrae image 166ii', and a third centroids 528 of the third vertebrae image 166iii'. Each of the centroids may be measured relative to one another to allow for determination of the closest pairwise position between the tracked vertebrae 166i and 166iii, and the second vertebrae 166*ii*. It is understood that other appropriate portions may be measured between the image portions, such as pedicles, spinous processes, or other appropriate determined or identified portions in the image. Further, as noted above, endplates of the vertebrae and/or geometries associated therewith such as lines or planes may be determined and illustrated. These may also be used to display and/or determine position and movement of the vertebra in the image 108. The navigation system may include appropriate instructions to segment and/or identify selected portions of the anatomy of the vertebrae in the image 108 and/or other appropriate portions for measuring comparative distances between image portions.

The navigation system 20 may also include information regarding which portions are directly tracked, such as either automatic or manual input as discussed above. Thus the closest portion or tracked portion to the untracked portion may be determined. For example, the navigation system may measure the distance between the first centroid 520 and the second centroid 524 and make a determination that it is the shortest distance. Accordingly, an inference may be made of the position of the second vertebrae 166*ii* relative to the first vertebrae 166*i* based upon the directly tracked position of the first vertebrae 166*i*.

The image 108 may therefore be updated with the selected position of the second vertebrae 166*ii* based upon the direct tracking of the closest vertebrae. For example, the position of the second vertebrae 166*ii* may assume to be moved from an initial or originally segmented position within a selected threshold of the directly tracked position of the closest vertebrae, such as having a translation movement (e.g. delta) of about 70% to about 90% of the directly tracked portion. In various embodiments, selected portions may be assumed to move or have a delta translation of exactly the same amount of a selected tracked portion. Thus, the second vertebra 166*ii* may be illustrated to move in the same amount and manner of the a selected vertebra, such as the vertebra 166*i*.

Further, a determined position of the untracked vertebrae 166*ii* may be based upon an interpolation between the two directly tracked vertebrae. For example, the position of the first vertebrae 166*i* is known directly from the first tracking device 160*i* and the precise position of the third vertebrae 166*iii* is known directly from the tracked position of the third tracking device 160*iii*. The position of the untracked vertebrae 166*ii* may be based upon a selected function of the known position of the two vertebrae on either side of the untracked vertebrae 166*ii*.

The interpolation function may be any appropriate function and may be determined by the user during a selected procedure and/or predetermined based upon a biomechanical model of the known or suspected movement of a vertebrae between two adjacent vertebrae, particularly in a selected portion of the anatomy. For example, the interpolation may be a direct interpolation, such as in a line or plane between the first vertebrae image 166*i*' and the third vertebrae image 166*iii*'. Thus, if the first vertebrae 166*ii* is tracked to a first angular orientation 540 and the third vertebrae 166*iii* is tracked to a second angular position 544, then an interpolated angular position of the second vertebrae 166*i* may be determined to be generally equal distance between the first angular position 540 and the second angular position 544 and generally determined to be at an angular position 548. The angular position 548 may be a first distance 552 and a second distance 554 from the second angular position 544. Thus, the third angular position 548 may be substantially between the first angular position 544 and the second angular position or line 544. According to various embodiments, spherical linear interpolation may be a specific method one might use to interpolate the rotational components of two different transforms.

Alternatively or in addition thereto, a biomechanical model may be used to determine and/or update or refine the interpolated or estimated position such as a model based upon known muscle or soft tissue interactions, range of motion limitations or determinations, or other appropriate known or determined biomechanical features. In various embodiments, the biomechanical features may include rigid body dynamics, collision response, Hooke's law or more advanced models of interaction based on empirically determined material properties (either general or patient-specific), finite element modeling, and any combination of the above.

As discussed above, with reference to FIGS. 11A and 11B, an untracked element or portion in the navigation space may have its position interpolated or determined between two tracked portions and/or relative to a single tracked portion. Similarly, an instrument may have a plurality of portions that may be positioned or movable relative to one another. In addition, an implant may include more than one portions, such as a pedicle screw and interconnecting rod, a multi-piece interventricular disc, a femoral implant and a tibia implant for a total knee replacement, or other implant systems. The position of a an untracked portion may be determined based upon tracking of a closest portion, interpolation between two tracked portions, and based upon determinations of selected or known moving ability of one piece relative to another. Accordingly, untracked portions of instruments may also be tracked when interpolated with a tracking system.

With reference to the figures above, and with exemplary reference to FIGS. 11A and 11B, the tracked portions of the navigation field may be used to update the display 84 of the image 108. It is understood that any appropriate portions may be viewed on the display which may include the vertebral portions, such as the first vertebrae 166*i* displayed as the vertebrae 166'. As the vertebrae 166*i* moves in the navigation space, its position may be updated on the display 84, such that the image 108 will change to show movement of the vertebral display portion 166*i*'. The movement can be determined based upon tracking the first tracking device 160*i* relative to a selected reference, such as the third tracking device 160*iii* and/or the patient tracker 58.

Movement of the vertebrae 166*i* may be in any appropriate translation or rotational position, for example including angular movement to an exemplary position, including 166*i*'*a*. When the display 84 is update and the image 108 is changed, the previous position of the implant portion 166*i*' may not appear such that only the presently tracked position of the vertebrae 166*i* is displayed. It is understood that other positions are also updated on the display 84, such as positions of the tracked instrument 68 may be displayed on the display as a graphical representation 68'.

Such changes may occur as implants or members are positioned in the subject 30, such as an intervertebral body 600, as illustrated in FIG. 11A. An intervertebral body may be moved or positioned between the first vertebrae 166*i* and the second vertebrae 166*ii*. The intervertebral body 600 may be displayed on the display device 84 relative to the image 108 as a graphical representation 600'. The graphical representation 600' of the intervertebral body 600 may be displayed based upon a tracked position of the intervertebral body 600 directly such as with a tracking member 604 positioned in the intervertebral body similar to that discussed above. Further, as the adjacent or contacted vertebrae and/or other appropriate portions are also tracked to the position of the vertebrae may also be illustrated on the display device 84.

Figure 12A:
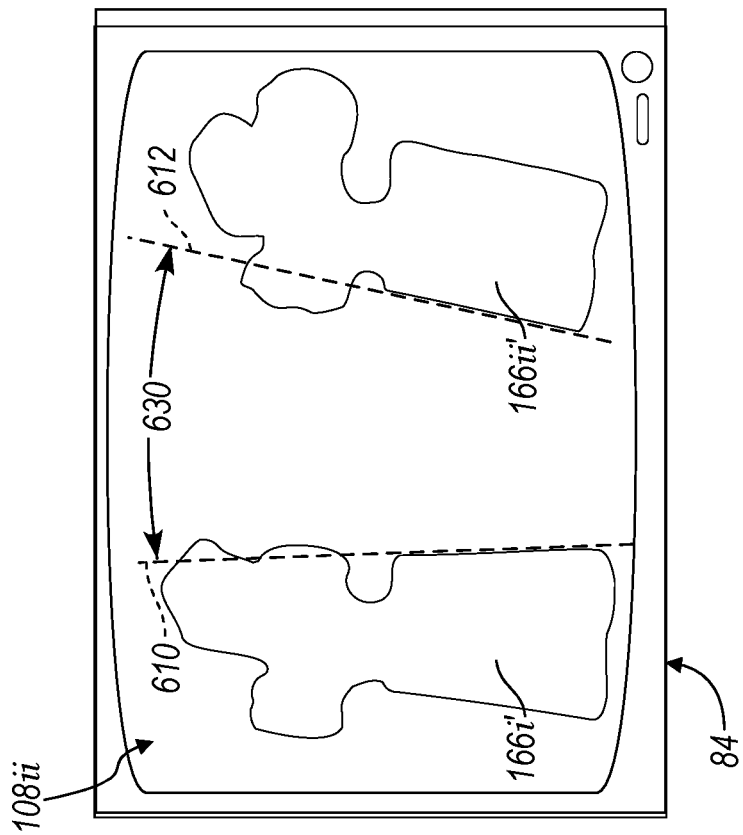
FIG. 12A is a display illustrating an image with tracked portions therein in a first relative position, according to various embodiments.
Figure 12B:
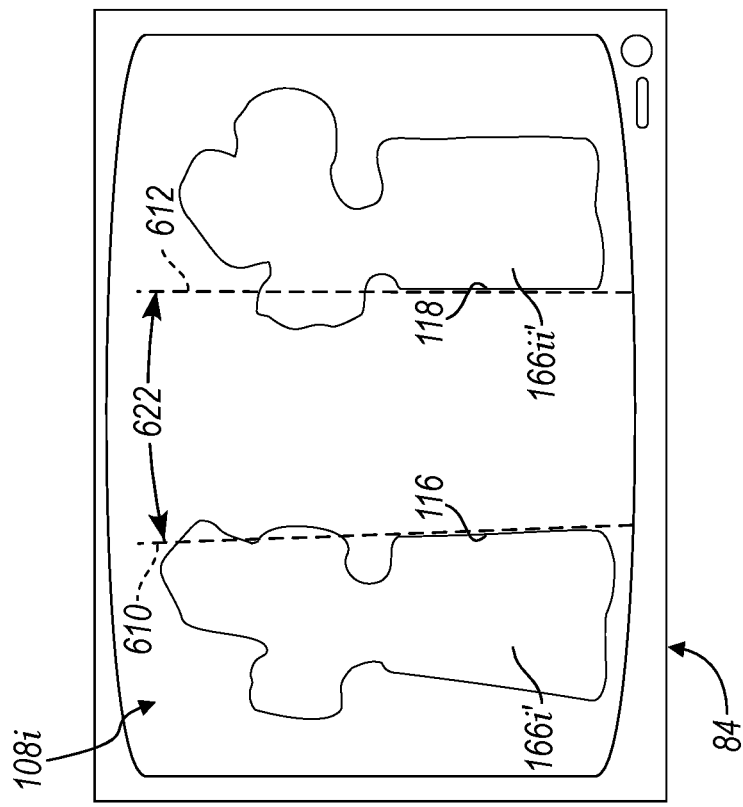
FIG. 12B is a display illustrating an image with tracked portions therein in a second relative position, according to various embodiments.

With continuing reference to FIGS. 11A and 11B and additional reference to FIGS. 12A and 12B, the display 84 may also be updated with selected images. For example, the image 108 may be updated overtime such as to illustrate or display the first image 108*i* and a second image 108*ii*. The second image 108*ii* may include a change of the displayed position of the vertebrae 166*i'* and 166*ii'* to show movement of the vertebrae relative to one another, implants positioned relative to the vertebrae, and other appropriate information.

For example, as illustrated in FIG. 12A lines 610 and 612 may represent respective endplates 616 and 618 of the respective vertebrae 166*i'* and 166*ii'*. As discussed above, the endplates and/or planes or lines may be determined due to segmentation and the lines 610, 612 may be also determined and then displayed in the image 108*i*. A first angle 622 may be displayed as determined between the lines 610, 612. After manipulation of the subject 30, such as movement of the vertebrae 166*i* and 166*ii*, the image may be updated as 108*ii* illustrated in FIG. 12B. The movement of the vertebrae 166 may be due to positioning of an implant, such as the intervertebral implant 600, illustrated in FIG. 11A, manual manipulation of the spine, implantation of a fusion system, or other appropriate changes. Nevertheless, the image 108*i* may include the lines 610 and 612 relative to the respective vertebrae 166*i'* and 166*ii'*.

A second angle 630 may be displayed between the two lines 610, 612. The second angle 613 may be analyzed for determination of a selected angle or comparison to a planned angle, an a priori angle, or other appropriate determination. For example, the user 72 may determine a desired angle or selected angle between the two vertebrae 166*i* and 166*ii* and the user may view the display 84 to determine whether the second angle 630 is the selected angle. If not, the manipulation of the vertebrae may be further performed in an attempt to achieve the selected angle.

Nevertheless, due to tracking of the individual vertebrae, the display 84 may display the image 108*ii* that is updated in substantially real time to view the position of the vertebrae 166*i*, 166*ii* as a representations 166*i'* and 166*ii'*. The representations of the vertebrae on the display may include the segmented images, as discussed above that are updated with the tracking devices associated therewith.

Further, as illustrated in FIG. 11A, the intervertebral body 600 may be positioned relative to selected portions of the anatomy, such as the second vertebrae 166*i*. The intervertebral implant 600 may include the tracking device 604. The implant 600, therefore, once implanted, may be determined to be positioned adjacent to the endplate vertebrae 166*ii*. Accordingly, the display, such as the display 11B and/or 12B, may be updated to illustrate the vertebrae image 166*ii* as being in contact with the intervertebral body 600. As illustrated in FIG. 11B, the graphical representation of the implant 600' may be displayed in contact with the vertebral representation 166*ii'* and the image 108 may be updated to illustrate the same even if the second vertebrae 166*ii* is not directly tracked. Due to the positioning of the implant 600 in contact with the vertebrae 166*ii*, the image 108 may be updated to illustrate the position of the vertebrae relative to the implant, such as in contact with the implant 600 by illustrating the vertebral display 166*ii'* in the image in contact with the graphical representation of the implant 600. Similarly, the second image 108*ii* in FIG. 12B may be updated due to positioning of an implant between the vertebrae 166*i* and the second vertebrae 166*ii*. Thus, the updated image may illustrated selected portions (e.g. graphical representations of instruments and/or portions of the image) in different or changes positions relative to a first image.

In various embodiments, the implant 600 may be an adjustable or expandable implant. It is understood that any appropriate implant may be an adjustable implant and the intervertebral body 600 is merely exemplary. Nevertheless, the intervertebral body 600 may be positioned between two vertebrae that may be directly tracked such as the first vertebrae 166*i* and the second vertebrae 166*ii*. Although not specifically illustrated in FIG. 11A, as discussed above all of the vertebrae of interest may be directly tracked with the tracking device as illustrated in FIG. 2. Thus, the intervertebral body 600 may be adjusted, such as adjusted to a maximum distance or dimension.

The tracked position of the first vertebra 166*i* to the second vertebra 166*ii* may be used to determine the efficacy of the implant 600 by measuring the amount of movement between the two vertebrae. For example, as illustrated in FIG. 12A the intervertebral body may be positioned between the two vertebrae 166*i* and 166*ii*. The angle or distance between the two lines 610, 612 representing the respective implants 616, 618 may be measured. The intervertebral body may then be adjusted and the distance between the two lines 610, 612 may then be measured and the image may be updated in the image 108*ii*. The user 72 may evaluate and/or the navigation system 20 may evaluate the difference in position and/or ultimate position between the two vertebrae 166*i* and 166*ii* in the image 108*ii* to determine the efficacy of the implant. For example, if the movement is not parallel, a selected angle has not been achieved, or other appropriate change has not been achieved due to the change of the implant 600 the user may evaluate the efficacy of the implant and/or select a new implant during a trial.

Accordingly, tracking the plurality of elements in the navigation field, such as in the subject 30, may be used for performing the procedure or any appropriate procedure relative to the subject 30. The tracking of the plurality of elements may be used to update the display 108 to confirm the efficacy of a selected portion of a procedure, position implant, or other appropriate information. Thus, tracking the plurality of portions in the navigation space may be used to confirm a procedure and/or assist in planning additional portions of a procedure, including a trail stage when selecting an appropriate or selected implant.

Further, by tracking all or a plurality of the members in the navigation space. The image 108 may be updated with substantially real time position of all of the elements in the region of interest (e.g. vertebrae) for a procedure. Thus, a more accurate position of an unconnected member, such as the instrument 68, may be navigated relative to members in the region of interest, such as the vertebrae. The display 84 displaying the image 108 may include substantially real time and precise positioning of the elements therein (e.g. segmented members, instruments, etc.) for performing a selected procedure. Moreover, the image 108 may be a direct image or generated image (such as based on x-ray image data). The portions of the image may be segmented therefrom, such as the individual vertebra. The image 108 may be updated by moving the segmented portions. The image 108 may also be updated by display and/or moving graphical representations of the imaged portions or other members (e.g. instruments).

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions (also referred as a computer program), which may result from or be derived from an algorithm as discussed above, may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of performing a navigated procedure relative to a subject, comprising:
    accessing first image data of at least a region of interest of the subject, wherein the first image data includes at least a first segmented portion, a second segmented portion, and a third segmented portion;
    tracking a first tracking device, wherein the first tracking device is connected to a first portion of the subject;
    tracking a second tracking device, wherein the second tracking device is connected to a second portion of the subject;
    associating the first tracking device with the first segmented portion in the first image data;
    associating the second tracking device with the second segmented portion in the first image data;
    determining a position of the third segmented portion relative to the first segmented portion and the second segmented portion;
    displaying the first image with a display device;
    updating the display of the first image, including changing a position of the first segmented portion or the second segmented portion based upon tracking the first tracking device connected to the first portion and tracking the second tracking device connected to the second portion or the third segmented portion based on the determined position of the third segmented portion;
    determining a greater confidence of tracking between the first tracking device and the second tracking device;
    tracking an instrument; and
    selecting the determined greater confidence of tracking between the first tracking device and the second tracking device as a reference for the tracking the instrument.

2. The method of claim 1, further comprising:
    segmenting the first image data to determine at least a boundary of the first segmented portion and the second segmented portion.

3. The method of claim 1, wherein associating the first tracking device with the first segmented portion in the first image data and associating the second tracking device with the second segmented portion in the first image data, comprises:
    inputting into a navigation system an identification of the first tracking device with the first segmented portion; and
    inputting into the navigation system an identification of the second tracking device with the second segmented portion.

4. The method of claim 1, wherein associating the first tracking device with the first segmented portion in the first image data and associating the second tracking device with the second segmented portion in the first image data, comprises:
    executing instructions with a navigation system to determine a position of the first tracking device relative to a known reference device and the first segmented portion; and
    executing instructions with the navigation system to determine a position of the second tracking device relative to the known reference device and the second segmented portion.

5. The method of claim 1, further comprising:
    forming a bore in the first portion of the subject with the instrument; and
    disengaging the first tracking device from the instrument within the bore to connect the first tracking device to the first portion of the subject.

6. The method of claim 1,
    wherein determining the position of the third segmented portion relative to the first segmented portion and the second segmented portion comprises determining a real time position of the third segmented portion of the subject; and
    updating the display of the first image to include a real time position of the third portion of the subject.

7. The method of claim 1, wherein determining the position of the third segmented portion relative to the first segmented portion and the second segmented portion comprises:
    interpolating between the first segmented portion and the second segmented portion based on the tracking of the first tracking device and the second tracking device.

8. The method of claim 1, wherein determining the position of the third segmented portion relative to the first segmented portion and the second segmented portion comprises:

accessing a biomechanical model of the third segmented portion relative to at least one of the first segmented portion or the second segmented portion; and
updating a real time position of the third segmented portion in the display of the first image based on the accessed biomechanical model of the third segmented portion, the tracking of the first tracking device, and the second tracking device.

9. The method of claim 1, further comprising:
selecting either of the first tracking device or the second tracking device as a subject reference to maintain a registration of the first image to a subject space based on tracking of the first tracking device and the second tracking device.

10. The method of claim 9, further comprising:
tracking a reference point of the subject by at least (i) the tracking the first tracking device and (ii) the tracking the second tracking device;
wherein the tracking the first tracking device is in a first coordinate system and the tracking the second tracking device is in a second coordinate system;
wherein both the first tracking device and the second tracking device are fixed relative to the reference point.

11. A method of performing a navigated procedure relative to a subject, comprising:
accessing a first image data of at least a region of interest of the subject, wherein the first image data includes at least a first segmented portion and a second segmented portion;
tracking a first tracking device, wherein the first tracking device is connected to a first portion of the subject;
tracking a second tracking device, wherein the second tracking device is connected to a second portion of the subject;
associating the first tracking device with the first segmented portion in the first image data;
associating the second tracking device with the second segmented portion in the first image data;
displaying the first image with a display device;
updating the first image, including changing a position of the first segmented portion or the second segmented portion based upon tracking the first tracking device connected to the first portion and tracking the second tracking device connected to the second portion;
determining a greater confidence of tracking between the first tracking device and the second tracking device;
tracking an instrument; and
selecting the determined greater confidence of tracking between the first tracking device and the second tracking device as a reference for the tracking the instrument.

12. A system to navigate a procedure relative to a subject, comprising:
a display device to display a first image having a first segmented portion and a second segmented portion;
a first tracking system defining a first tracking space with a first coordinate system;
a first tracking device trackable in the first coordinate system, wherein the first tracking device is associated with the first segmented portion in the first image data;
a second tracking device trackable in the first coordinate system, wherein the second tracking device is associated with the second segmented portion in the first image data; and
a navigation processor system operable to:
register a first image data coordinate system of the first image data to the first coordinate system;
track the first tracking device;
track the second tracking device;
associate the first tracking device with the first segmented portion in the first image data;
associate the second tracking device with the second segmented portion in the first image data;
determine a position of a third segmented portion in the first image data relative to the first tracking device or the second tracking device;
update the first image, including changing a position of the first segmented portion, the second segmented portion, or the third segmented portion based upon tracking the first tracking device and tracking the second tracking device and the determined position of the third segmented portion, and
generate the updated first image for display with the display device;
an instrument tracked with the first tracking system;
wherein the navigation processor system is further operable to:
determine a greater confidence of tracking between the first tracking device and the second tracking device; and
select the determined greater confidence of tracking between the first tracking device and the second tracking device as a reference for the tracking the instrument.

13. The system of claim 12, wherein the navigation processor system associates the first tracking device with the first segmented portion in the first image data and associates the second tracking device with the second segmented portion in the first image data based at least on a user input.

14. The system of claim 12,
wherein the instrument is configured to perform a portion of a procedure on the subject;
wherein the first tracking device is separable from the instrument;
wherein the first tracking device is configured to remain fixed to a first portion of the subject after performing the portion of the procedure;
wherein the first portion of the subject is represented in the first image as the first segmented portion in the first image data.

15. The system of claim 12, wherein the navigation processor system is further operable to:
access a biomechanical model of the third segmented portion relative to at least one of the first segmented portion or the second segmented portion; and
update a real time position of the third segmented portion in the generated updated first image based on the accessed biomechanical model of the third segmented portion, the tracking of the first tracking device, and the tracking of the second tracking device.

16. The system of claim 12, wherein the navigation processor system is further operable to determine measurements relative to at least two of the first segmented portion, the second segmented portion, or the third segmented portion.

17. A system to navigate a procedure relative to a subject, comprising:
a display device to display a first image having a first segmented portion and a second segmented portion;
a first tracking system defining a first tracking space with a first coordinate system;
a first tracking device trackable in the first coordinate system, wherein the first tracking device is associated with the first segmented portion in the first image data;

a second tracking device trackable in the first coordinate system, wherein the second tracking device is associated with the second segmented portion in the first image data; and a navigation processor system operable to:
- register a first image data coordinate system of the first image data to the first coordinate system;
- associate the first tracking device with the first segmented portion in the first image data;
- associate the second tracking device with the second segmented portion in the first image data;
- update the first image, including changing a position of the first segmented portion or the second segmented portion, based upon tracking the first tracking device and tracking the second tracking device, and
- generate the updated first image for display with the display device; and an instrument tracked with the first tracking system;

wherein the navigation processor system is further operable to:
- determine a greater confidence of tracking between the first tracking device and the second tracking device; and
- select the determined greater confidence of tracking between the first tracking device and the second tracking device as a reference for the tracking the instrument.

* * * * *

UNITED STATES PATENT AND TRADEMARK OFFICE
CERTIFICATE OF CORRECTION

PATENT NO. : 11,426,242 B2
APPLICATION NO. : 16/261882
DATED : August 30, 2022
INVENTOR(S) : Victor D. Snyder et al.

It is certified that error appears in the above-identified patent and that said Letters Patent is hereby corrected as shown below:

On the Title Page

Item (56), Page 2, Column 2, Line 15, delete "Patenability" and insert --Patentability-- therefor In the Specification Column 5, Line 58, delete "80" and insert --30-- therefor Column 6, Line 28, delete "80" and insert --30-- therefor Column 6, Line 40, delete "92" and insert --94-- therefor Column 7, Line 52, delete "reference," and insert --reference.-- therefor Column 13, Line 44, delete "580." and insert --58$o$.-- therefor Column 15, Line 61, delete "580." and insert --58$o$.-- therefor Column 17, Line 14, delete "64." and insert --84.-- therefor Column 22, Line 5, delete "10," and insert --30,-- therefor Column 22, Line 16, delete "166$i$." and insert --166$ii$.-- therefor Column 24, Line 9, delete "infra-red)" and insert --infra-red))-- therefor Column 24, Line 37, delete "78" and insert --72-- therefor Column 26, Line 54, delete "166$iii$." and insert --166$ii$.-- therefor Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,426,242 B2

Column 27, Line 57, delete "166*ii*." and insert --166*i*.-- therefor

Column 27, Line 60, delete "166*i*" and insert --166*ii*-- therefor

Column 27, Line 67, delete "544" and insert --540-- therefor

Column 29, Line 31, delete "613" and insert --630-- therefor

Column 29, Line 49, delete "166*i*." and insert --166*ii*.-- therefor